(12) United States Patent
Kuchenbeiser et al.

(10) Patent No.: US 10,570,513 B2
(45) Date of Patent: Feb. 25, 2020

(54) ORGANOSILANE PRECURSORS FOR ALD/CVD SILICON-CONTAINING FILM APPLICATIONS AND METHODS OF USING THE SAME

(71) Applicants: American Air Liquide, Inc., Fremont, CA (US); Glenn Kuchenbeiser, Newark, DE (US); Claudia Fafard, Newark, DE (US)

(72) Inventors: Glenn Kuchenbeiser, Newark, DE (US); Claudia Fafard, Newark, DE (US)

(73) Assignee: American Air Liquide, Inc., Fremont, CA (US)

( * ) Notice: Subject to any disclaimer, the term of this patent is extended or adjusted under 35 U.S.C. 154(b) by 218 days.

(21) Appl. No.: 15/535,631

(22) PCT Filed: Dec. 10, 2015

(86) PCT No.: PCT/US2015/065077
§ 371 (c)(1),
(2) Date: Jun. 13, 2017

(87) PCT Pub. No.: WO2016/094711
PCT Pub. Date: Jun. 16, 2016

(65) Prior Publication Data
US 2018/0355483 A1 Dec. 13, 2018

Related U.S. Application Data

(60) Provisional application No. 62/091,489, filed on Dec. 13, 2014.

(51) Int. Cl.
| | | |
|---|---|---|
| *C23C 16/30* | (2006.01) | |
| *C23C 16/455* | (2006.01) | |
| *C07F 7/02* | (2006.01) | |
| *C09D 4/00* | (2006.01) | |
| *C23C 16/50* | (2006.01) | |
| *C23C 16/56* | (2006.01) | |

(52) U.S. Cl.
CPC ........ *C23C 16/45553* (2013.01); *C07F 7/025* (2013.01); *C09D 4/00* (2013.01); *C23C 16/30* (2013.01); *C23C 16/50* (2013.01); *C23C 16/56* (2013.01)

(58) Field of Classification Search
None
See application file for complete search history.

(56) References Cited

U.S. PATENT DOCUMENTS

| | | |
|---|---|---|
| 3,355,477 A | 11/1967 | Frye |
| 4,841,084 A | 6/1989 | Corriu et al. |
| 6,391,803 B1 | 5/2002 | Kim et al. |
| 6,465,387 B1 | 10/2002 | Pinnavaia et al. |
| 6,736,993 B1 | 5/2004 | Xu et al. |
| 6,869,638 B2 | 3/2005 | Baum et al. |
| 7,125,582 B2 | 10/2006 | McSwiney et al. |
| 7,192,626 B2 | 3/2007 | Dussarrat et al. |
| 7,332,618 B2 | 2/2008 | Meiere |
| 7,482,286 B2 | 1/2009 | Misra et al. |
| 7,875,312 B2 | 1/2011 | Thridandam et al. |
| 8,129,555 B2 | 3/2012 | Cheng et al. |
| 8,828,505 B2 | 9/2014 | Thridandam et al. |
| 2006/0045986 A1 | 3/2006 | Hichberg et al. |
| 2006/0258173 A1 | 11/2006 | Xiao et al. |
| 2007/0160774 A1 | 7/2007 | Tsukada et al. |
| 2007/0275166 A1 | 11/2007 | Thridandam et al. |
| 2009/0302434 A1 | 12/2009 | Pallem et al. |
| 2010/0112211 A1* | 5/2010 | Xu ........................ C07C 211/65 427/248.1 |
| 2010/0164057 A1 | 7/2010 | Hunks et al. |
| 2010/0317150 A1 | 12/2010 | Hunks et al. |
| 2011/0045676 A1 | 2/2011 | Park et al. |
| 2011/0250354 A1 | 10/2011 | Pallem et al. |
| 2012/0277457 A1 | 11/2012 | Lehmann et al. |
| 2013/0022745 A1 | 1/2013 | Dussarrat et al. |
| 2013/0078392 A1 | 3/2013 | Xiao et al. |
| 2014/0031502 A1 | 1/2014 | Qin et al. |
| 2015/0087139 A1 | 3/2015 | O'Neill et al. |

FOREIGN PATENT DOCUMENTS

| | | | |
|---|---|---|---|
| CN | 104341447 | 2/2015 | |
| CN | 104447838 | 3/2015 | |
| EP | 2 154 141 | 2/2010 | |
| EP | 1 563 117 | 6/2010 | |
| EP | 2 392 691 | 12/2011 | |
| EP | 2 444 405 | 4/2012 | |
| JP | H06 132276 | 5/1994 | |
| JP | H06 132284 | 5/1994 | |
| JP | 2000 195801 | 7/2000 | |
| JP | 2010 514918 | 5/2010 | |
| KR | 2012 0060843 | 6/2012 | |
| KR | 10 2012 0078909 | 7/2012 | |
| WO | WO 2005 093126 | 10/2005 | |
| WO | WO-2005093126 A1 * | 10/2005 | ........... C23C 16/308 |
| WO | WO 2006 097525 | 9/2006 | |
| WO | WO 2006 136584 | 12/2006 | |
| WO | WO 2008 057616 | 5/2008 | |
| WO | WO 2009 087609 | 7/2009 | |
| WO | WO 2011 103282 | 8/2011 | |
| WO | WO 2011 123792 | 10/2011 | |

(Continued)

OTHER PUBLICATIONS

ISA Written Opinion—PCT/US2015/065077 (Year: 2015).*

(Continued)

*Primary Examiner* — Clinton A Brooks
*Assistant Examiner* — Kofi Adzamli
(74) *Attorney, Agent, or Firm* — Patricia E. McQueeney; Yan Jiang

(57) ABSTRACT

Disclosed are organosilane precursors, methods of synthesizing the same, and methods of using the same to deposit silicon-containing films using vapor deposition processes. The disclosed organosilane precursors have the following formula: $SiH_x(RN-(CR)_n-NR)_y(NRR)_z$ wherein R may each independently be H, a $C_1$ to $C_6$ alkyl group, or a $C_3$-$C_{20}$ aryl or heterocycle group, $x+y+z=4$ and n, x, y and z are integers, provided that $x \neq 3$ when $y=1$. Preferably, $n=1$ to 3, $x=0$ to 2, $y=1$ to 2, and $z=1$ to 3.

15 Claims, No Drawings

(56) References Cited

FOREIGN PATENT DOCUMENTS

| WO | WO 2012 176988 | 12/2012 |
|----|----------------|---------|
| WO | WO 2013 117326 | 11/2013 |
| WO | WO 2014 015232 | 1/2014 |
| WO | WO 2014 015237 | 1/2014 |
| WO | WO 2015 009997 | 1/2015 |

OTHER PUBLICATIONS

Asay,M. et al., "N-heterocyclic carbene analogues with low-valent Group 13 and Group 14 elements: syntheses, structures, and reactivities of a new generation of multitalented ligands," Chem. Rev. 2011, 111, 354-396.
Beckmann, J. et al., "The origin of ring strain and conformational flexibility in tri- and tetrasiloxane rings and their heavier Group 14 congeners," Organosilicon Chemistry VI: From Molecules to Materials, N. Auner and J. Weis, eds., 2005, Wley-VCH Verlag GmbH, Weinheim, 252-258.
Chult, C. et al., "Reactivity of penta- and hexacoordinate silicon compounds and their role as reaction intermediates," Chem. Rev. 1993, 93, 1371-1448.
Dona, N. et al., "Novel dimeric pentacoordinate silicon complexes: unusual reactivity of electron-rich aminosilane intermediates," Organosilicon Chemistry VI: From Molecules to Materials, N. Auner and J. Weis, eds., 2005, Wiley-VCH Verlag GmbH, Weinheim, 271-278.
Dransfeld, A. et al., "The effect of silyl anion substituents on the stability and NMR characteristics of cyclic polyphosphines—an ab initio-NMR Study," Organosilicon Chemistry VI: From Molecules to Materials, N. Auner and J. Weis, eds., 2005, Wley-VCH Verlag GmbH, Weinheim, 240-244.
Ebsworth, E.A.V. et al., "The preparation and properties of some silyl esters," J. Chem. Soc. (A), 1967, 69-72.
Eilingsfeld, H. et al., "Synthesen mit Amidchloriden, III. Synthese und Reaktionen von Chlorformamidiniumchloriden," Chemische Berichte vol. 97, Issue 5, May 1964, 1232-1245.
Von Frantzius, G. et al., "Strong evidence for an unconventional 1,2-(C->P)-silyl migration: DFT structures and bond strengths (compliance constants)," Organosilicon Chemistry VI: From Molecules to Materials, N. Auner and J. Weis, eds., 2005, Wley-VCH Verlag GmbH, Weinheim, 211-215.
Gonzalez-Garcia et al., "Pentacoordinate mono(β-diketonato)- and hexacoordinate bis-(β-diketonato)-silicon(IV) complexes obtained from (thiocyanato-N)hydridosilanes," Polyhedron 41 (2012), 127-133.
Hassler, K. et al., "Preparations and x-ray structures of some silicon-phosphorus and silicon-arsenic cages," Organosilicon Chemistry VI: From Molecules to Materials, N. Auner and J. Weis, eds., 2005, Wiley-VCH Verlag GmbH, Weinheim, 228-232.
Herzog, U. et al., "Si NMR chemical shift tensors in organosilicon chalcogenides," Organosilicon Chemistry VI: From Molecules to Materials, N. Auner and J. Weis, eds., 2005, Wiley-VCH Verlag GmbH, Weinheim, 259-264.
Ionescu, E. et al., "Strong evidence for an unconventional 1,2-(C->P)-silyl migration: formation and reactions of a P-silyl phosphaalkene complex," Organosilicon Chemistry VI: From Molecules to Materials, N. Auner and J. Weis, eds., 2005, Wiley-VCH Verlag GmbH, Weinheim, 202-208.
Junold, K. et al., "Bis[N,N'-diisopropylbenzamidinato(-)]silicon(II): a silicon(II) compound with both a bidentate and a monodentate amidinato ligand," Angew. Chem. Int. Ed. 2012, 51, 7020-7023.
Junold, K. et al., "Novel neutral hexacoordinate benzamidinatosilicon(IV) complexes with $SiN_3OF_2$, $SiN_3OCl_2$, $SiN_3OBr_2$, $SiN_5O$ and $SiN_3O_3$ skeletons," Dalton Trans., 2011, 40, 9844-9857.

Lange, H. et al., "Hypersilyltelluro-substituted silanes and $(Ph_2SiTe)_3$," Organosilicon Chemistry VI: From Molecules to Materials, N. Auner and J. Weis, eds., 2005, Wiley-VCH Verlag GmbH, Weinheim, 265-270.
Karsch, H.H. et al., "Bis(amidinate) complexes of silicon and germanium," Eur. J. Inorg. Chem. 1998, 433-436.
Karsch, H.H. et al., "'Hypervalent' molecules—low valency candidates for materials?," Organosilicon Chemistry VI: From Molecules to Materials, N. Auner and J. Weis, eds., 2005, Wiley-VCH Verlag GmbH, Weinheim, 194-284.
Karsch, H.H. et al., "Silicon and germanium amidinates," Organosilicon Chemistry IV: From Molecules to Materials, N. Auner and J. Weis, eds., Wiley-VCH Verlag GmbH, Weinheim, Germany, 287-293.
Karsch, H.H. et al., "Silicon and germanium compounds with amidinate ligands," Organosilicon Chemistry V: From Molecules to Materials, N.. Auner and J. Weis, eds., 2003, Wiley-VCH Verlag GmbH, Weinheim, 270-276.
Kliem, S. et al., "Silyl group migrations between oxygen and nitrogen in aminosiloxanes," Organosilicon Chemistry VI: From Molecules to Materials, N. Auner and J. Weis, eds., 2005, Wiley-VCH Verlag GmbH, Weinheim, 216-221.
Kost, D. et al., "Hydrazide-based hypercoordinate silicon compounds," Advancese in Organometallic Chemistry, 2004, vol. 50, 1-106.
Mehring, M. et al., "Homo- and heterometallic bismuth silanolates," Organosilicon Chemistry VI: From Molecules to Materials, N. Auner and J. Weis, eds., 2005, Wley-VCH Verlag GmbH, Weinheim, 233-239.
Mück, F.M. et al., "Donor-stabilized silylenes with guanidinato ligands," Eur. J. Inorg. Chem. 2013, 5821-5825.
Negrebetsky, V.V. et al., "Dynamic stereochemistry of hypervalent silicon, germanium and tin compounds containing amidomethyl C,O-chelating ligands," Russian Chemical Bulleting, vol. 46, No. 11, Nov. 1997, 1807-1831.
Pietschnig, R. et al., "Terphenyl phosphanosilanes," Organosilicon Chemistry VI: From Molecules to Materials, N. Auner and J. Weis, eds., 2005, Wiley-VCH Verlag GmbH, Weinheim, 222-227.
Siddiqi, K.S. et al., "Group IV metal complexes of the dithiocarbamate ligand derived from propanediamine," Synthesis and Reactivity in Inorganic and Metal-Organic chemistry, 23:5, 685-693.
Veith, M. et al., "Silanols as precursors to cyclo- and polysiloxanes," Organosilicon Chemistry VI: From Molecules to Materials, N. Auner and J. Weis, eds., 2005, Wiley-VCH Verlag GmbH, Weinheim, 245-251.
Wagler, J. et al., "Unique switching of coordination number with imine and enamine complexes of Group 14 elements," Organosilicon Chemistry VI: From Molecules to Materials, N. Auner and J. Weis, eds., 2005, Wiley-VCH Verlag GmbH, Weinheim, 279-284.
Weidenbruch, M., "A stable silylenoid and a donor-stabilized chlorosilylene: low-coordinate silicon compounds—a never-ending story?," Angew. Chem. Int. Ed. 2006, 45, 4241-4242.
Xu, C. et al., "Synthesis and characterization of neutral cis-hexacoordinate bis(β-diketonate) silicon(IV) complexes," Inorganic Chemistry 2004, 43, 1568-1573.
International Search Report and Written Opinion for related PCT/US2013/051244, dated Oct. 16, 2013.
International Search Report and Written Opinion for related PCT/US2013/051249, dated Oct. 16, 2013.
International Search Report and Written Opinion for related PCT/US2014/047154, dated Sep. 29, 2014.
International Search Report and Written Opinion for corresponding PCT/US2015/065077, dated Aug. 10, 2016.
Bombicz, P. et al., Neutral pentacoordinate Group 14 compounds with β-diketonato ligands, Organometallics, 2010, 29, 1100-1106.

* cited by examiner

ORGANOSILANE PRECURSORS FOR ALD/CVD SILICON-CONTAINING FILM APPLICATIONS AND METHODS OF USING THE SAME

CROSS REFERENCE TO RELATED APPLICATIONS

This application is a 371 of International PCT Application PCT/US2015/065077, filed Dec. 10, 2015, which claims priority to U.S. Provisional Patent Application No. 62/091,489 filed Dec. 13, 2014, the entire contents of which are incorporated herein by reference.

TECHNICAL FIELD

Disclosed are Si-containing film forming precursors, methods of synthesizing the same, and methods of using the same to deposit silicon-containing films using vapor deposition processes for manufacturing semiconductors, photovoltaics, LCD-TFT, flat panel-type devices, refractory materials, or aeronautics.

BACKGROUND

Si-containing thin films are used widely in the semiconductor, photovoltaic, liquid-crystal display-thin-film transistor (LCD-TFT), flat panel-type device, refactory material, or aeronautic industries. Si-containing thin films may be used, for example, as dielectric materials having electrical properties which may be insulating ($SiO_2$, SiN, SiCN, SiCOH, $MSiO_x$, wherein M is Hf, Zr, Ti, Nb, Ta, or Ge and x is greater than zero), Si-containing thin films may be used as conducting films, such as metal silicides or metal silicon nitrides. Due to the strict requirements imposed by downscaling of electrical device architectures towards the nanoscale (especially below 28 nm node), increasingly fine-tuned molecular precursors are required which meet the requirements of volatility (for Atomic layer deposition (ALD) process), lower process temperatures, reactivity with various oxidants and low film contamination, in addition to high deposition rates, conformality and consistency of films produced.

Organoaminosilanes have been used as precursors for CVD of Si-containing films. U.S. Pat. No. 7,192,626 to Dussarrat et al. discloses the use of trisilylamine $N(SiH_3)_3$ for deposition of SiN films. Other organoaminosilane precursors include diisopropylaminosilane [$SiH_3(NiPr_2)$] and analogous $SiH_3(NR_2)$ compounds disclosed in, for example, U.S. Pat. No. 7,875,312 to Thridandam et al. and phenylmethylaminosilane [$SiH_3(NPhMe)$] and related substituted silylanilines disclosed in, for example, EP 2392691 to Xiao et al.

WO2006/097525 to Dussarrat et al. disclosed another related class of Si precursors for CVD of Si-containing films given by a general formula $(R^1R^2N)_xSiH_{4-x}$ wherein x is an integer between 1 and 4 and the substituent R is H, $C_1$-$C_6$ linear, branched, or cyclic carbon chains.

Hunks et al. disclose a wide range of Si-containing precursors in US2010/0164057, including silicon compounds having the formula $R_{4-x}SiL_x$, wherein x is an integer having a value from 1 to 3, R may be selected from the group consisting of H, branched and unbranched $C_1$-$C_6$ alkyl, $C_3$-$C_8$ cycloalkyl, and $C_6$-$C_{13}$ aryl groups, and L may be selected from the group consisting of isocyanato, methylethylketoxime, trifluoroacetate, triflate, acyloxy, β-diketiminate, β-di-iminate, amidinate, guanidinate, alkylamino, hydride, alkoxide, or formate ligands. Pinnavaia et al. claim a method for the preparation of a porous synthetic, semicrystalline hybrid organic-inorganic silicon oxide composition from silicon acetylacetonate and silicon 1,3-diketonate precursors (U.S. Pat. No. 6,465,387).

Recently Dussarrat et al. disclosed silicon amidinate precursors in WO2014/015232 A1 having the form $H_3Si$ (amd) and silicon β-diketiminate precursors in WO2014015237 A1.

Despite the wide range of choices available for the deposition of Si containing films, additional precursors are continuously sought to provide device engineers the ability to tune manufacturing process requirements and achieve films with desirable electrical and physical properties.

SUMMARY

Disclosed are organosilane precursor compositions comprising a compound having the formula:

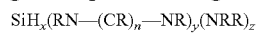

wherein R may each independently be H, a $C_1$ to $C_6$ alkyl group, or a $C_3$-$C_{20}$ aryl or heterocycle group, n, x, y and z are integers and x+y+z=4, provided that x≠3 when y=1. Preferably, n=1 or 3, x=0 to 2, y=1 to 2, and z=1 to 3.

The disclosed organosilane precursor compositions may have one or more of the following aspects:
- When n=1, x=1 or 2, y=1 or 2, and z=1 or 2, the precursor molecule contains amidinate, amido and hydride functional groups;
- When n=3, x=1 or 2, y=1 or 2, and z=1 or 2, the precursor molecule contains β-diketiminate, amido and hydride functional groups;
- x≠3 when y=1;
- n=1;
- x=2;
- y=1;
- z=1;
- the compound having the formula:

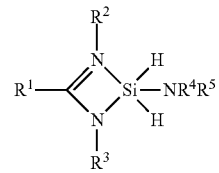

$R^1$ and $R^2$ and/or $R^1$ and $R^3$ and/or $R^4$ and $R^5$ being joined to form cyclic chains;

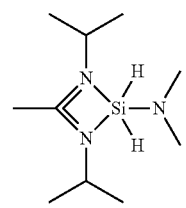

the compound being:

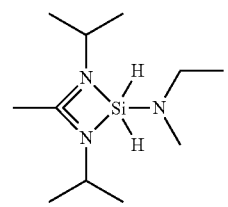

the compound being:
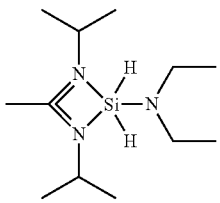
the compound being:
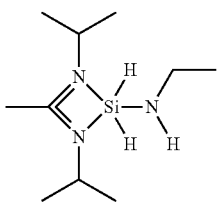
the compound being:
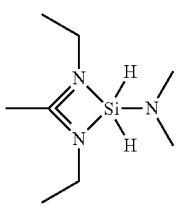
the compound being:
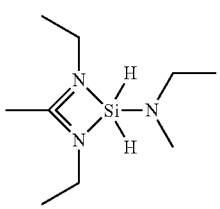
the compound being:
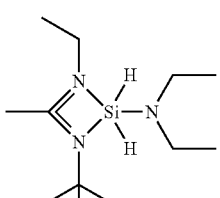
the compound being:
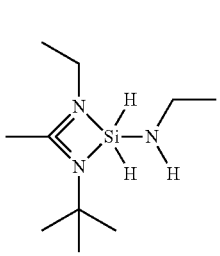
the compound being:
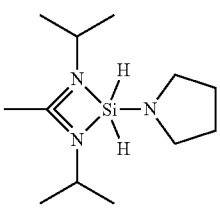
the compound being:
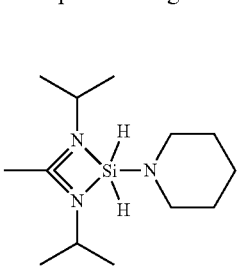
the compound being:
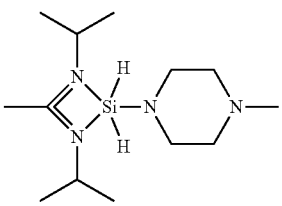
the compound being:
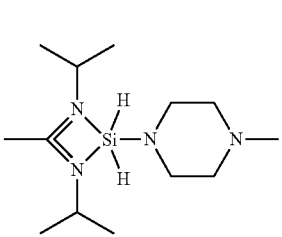
x=1;
z=2;
the compound having the formula:
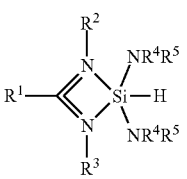
$R^1$ and $R^2$ and/or $R^1$ and $R^3$ and/or $R^4$ and $R^5$ being joined to form cyclic chains;

the compound being:
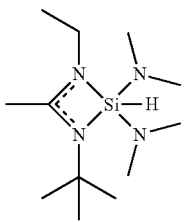
the compound being:
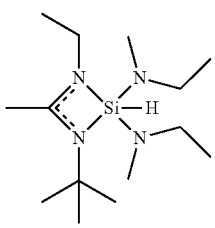
the compound being:
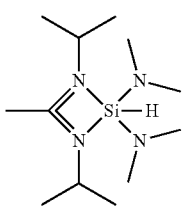
the compound being:
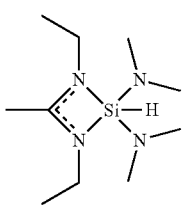
the compound being:
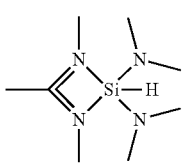
the compound being:
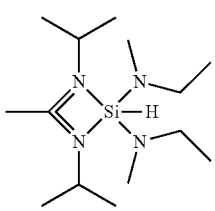
the compound being:
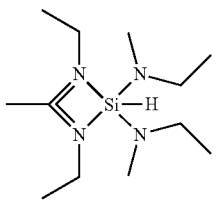
the compound being:
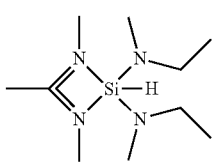
the compound being:
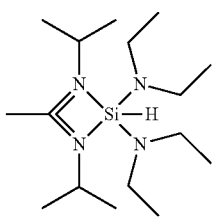
the compound being:
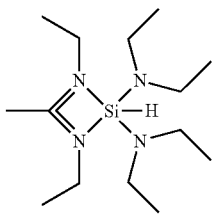
the compound being:
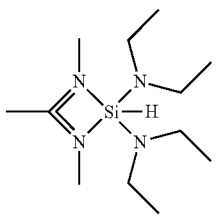
the compound being:
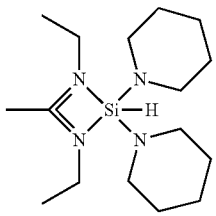

the compound being:
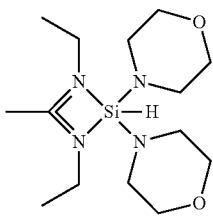
the compound being:
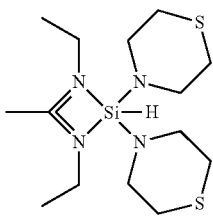
the compound being:
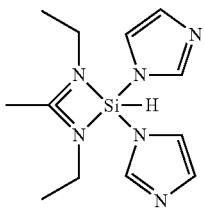
the compound being:
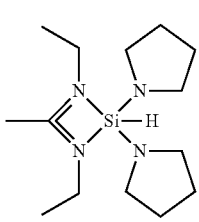
the compound being:
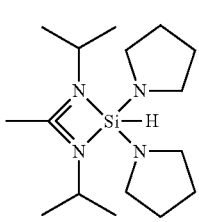
x=0;
z=3;
the compound having the formula:
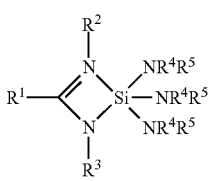
$R^1$ and $R^2$ and/or $R^1$ and $R^3$ and/or $R^4$ and $R^5$ being joined to form cyclic chains;
the compound being:
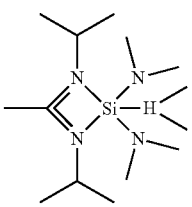
the compound being:
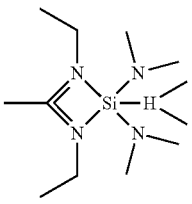
the compound being:
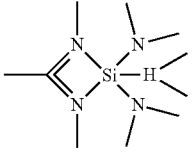
the compound being:
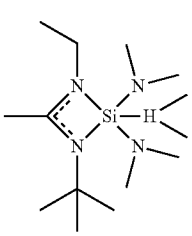
the compound being:
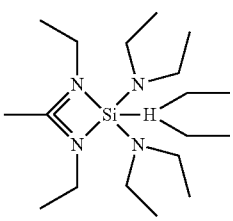
the compound being:
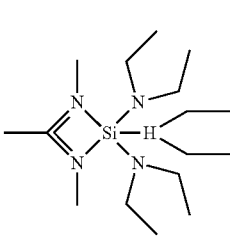

the compound being:
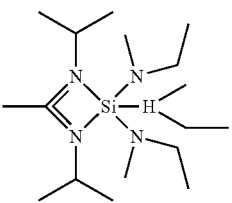
the compound being:
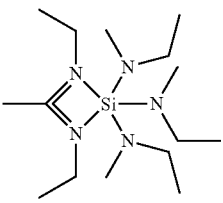
the compound being:
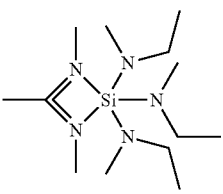
the compound being:
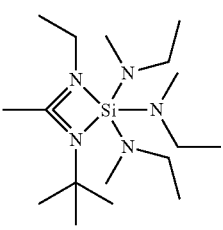
the compound being:
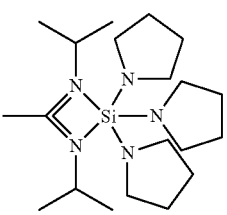
the compound being:
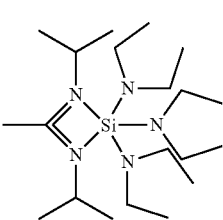
the compound being:
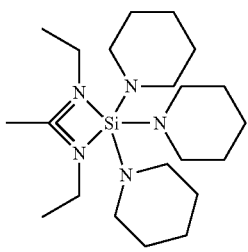
the compound being:
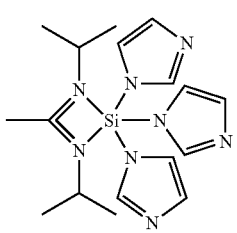
the compound being:
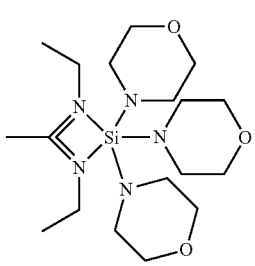
the compound being:
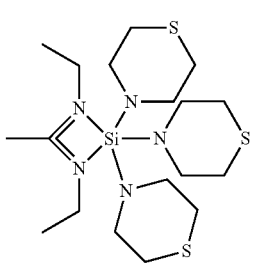
n=3;
x=2;
z=1;
the compound having the formula:
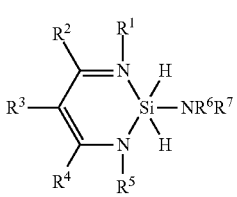

R[1] and R[2] and/or R[2] and R[3] and/or R[3] and R[4] and/or R[4] and R[5] and/or R[e] and R[7] being joined to form cyclic chains;
the compound being:
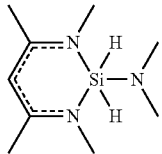
the compound being:
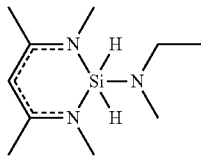
the compound being:
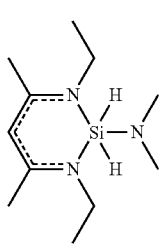
the compound being:
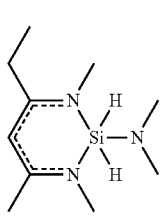
the compound being:
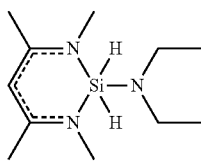
the compound being:
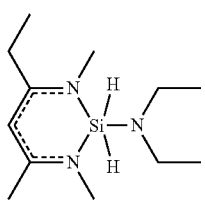
the compound being:
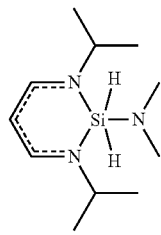
the compound being:
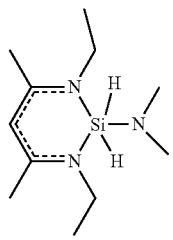
the compound being:
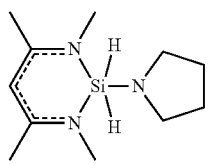
the compound being:
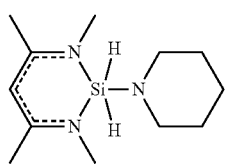
the compound being:
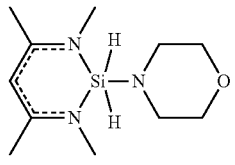
the compound being:
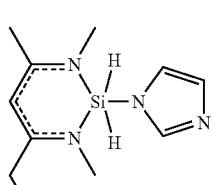
x=1;
z=2;

the compound having the formula:
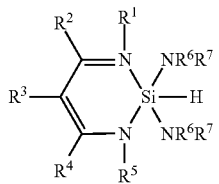
R¹ and R² and/or R² and R³ and/or R³ and R⁴ and/or R⁴ and R⁵ and/or R⁶ and R⁷ being joined to form cyclic chains;
the compound being:
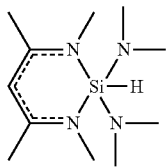
the compound being:
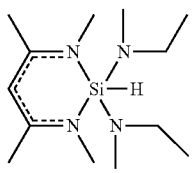
the compound being:
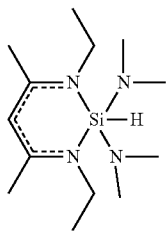
the compound being:
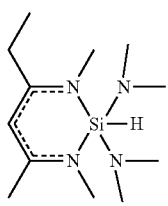
the compound being:
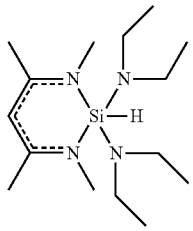
the compound being:
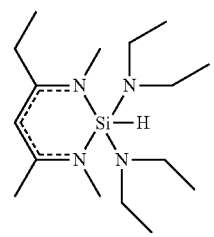
the compound being:
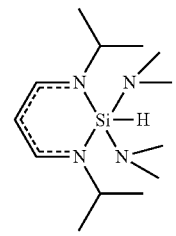
the compound being:
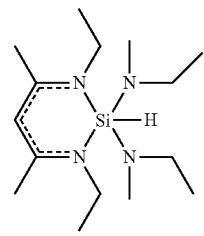
the compound being:
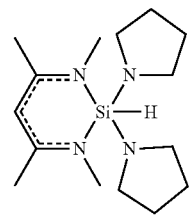
the compound being:
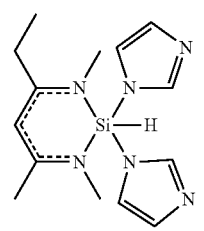
x=0;
z=3;

the compound having the formula:

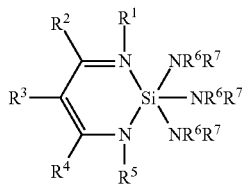

$R^1$ and $R^2$ and/or $R^2$ and $R^3$ and/or $R^3$ and $R^4$ and/or $R^4$ and $R^5$ and/or $R^6$ and $R^7$ being joined to form cyclic chains;

the compound being:

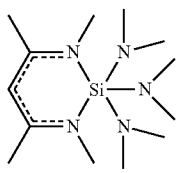

the compound being:

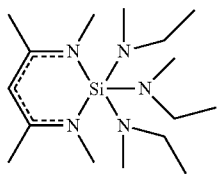

the compound being:

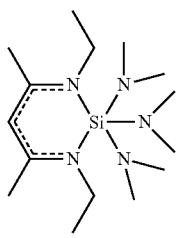

the compound being:

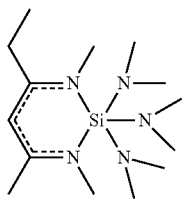

the compound being:

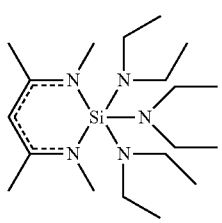

the compound being:

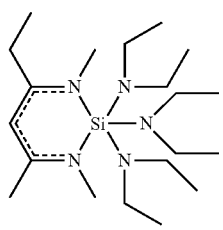

the compound being:

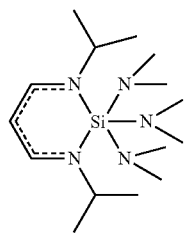

the compound being:

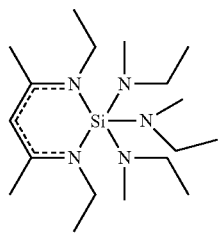

the compound being:

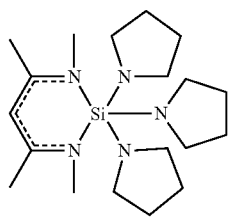

the compound being:

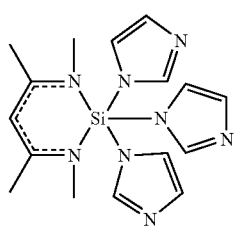

n=1;
x=1;
y=2;
z=1;

the compound having the formula:

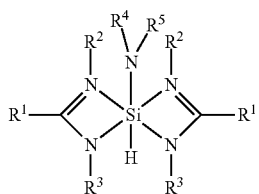

R¹ and R² and/or R¹ and R³ and/or R⁴ and R⁵ being joined to form cyclic chains;
the compound being:

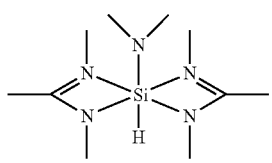

the compound being:

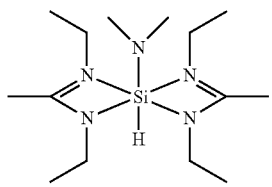

the compound being:

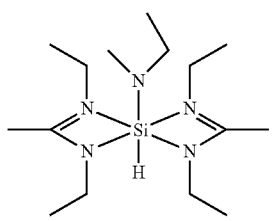

the compound being:

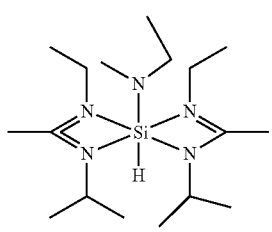

the compound being:

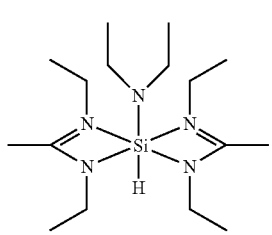

the compound being:

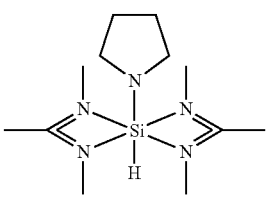

the compound being:

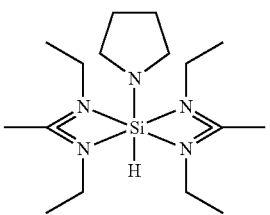

the compound being:

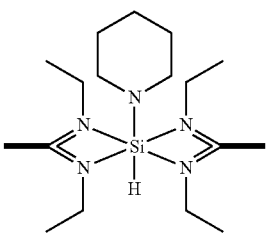

the compound being

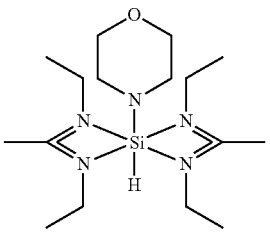

x=0;
z=2;
the compound having the formula:

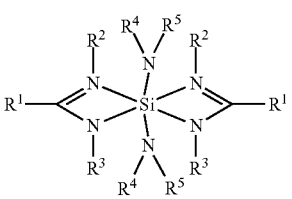

R¹ and R² and/or R¹ and R³ and/or R⁴ and R⁵ being joined to form cyclic chains;

the compound being:
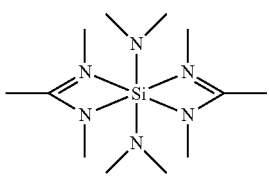
the compound being:
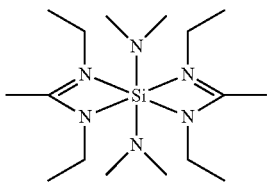
the compound being:
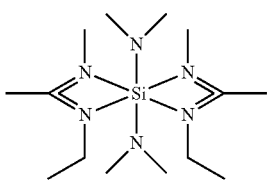
the compound being:
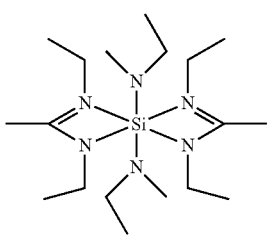
the compound being:
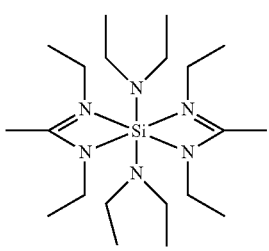
the compound being:
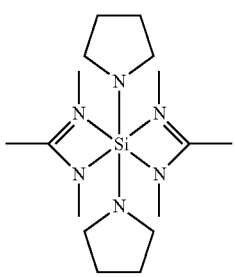
the compound being:
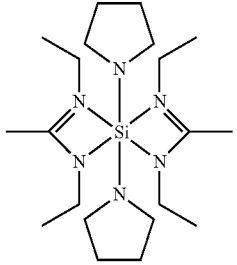
the compound being:
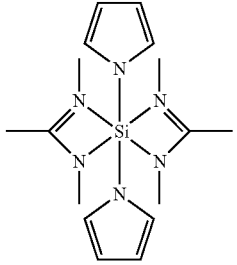
the compound being:
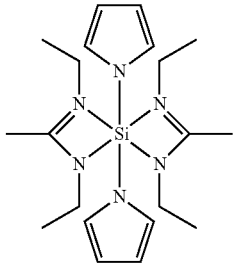
the compound being:
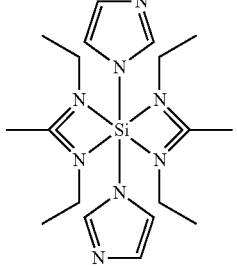
the compound being:
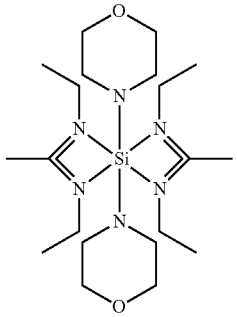
n=3;
x=1;
z=1;

the compound having the formula:

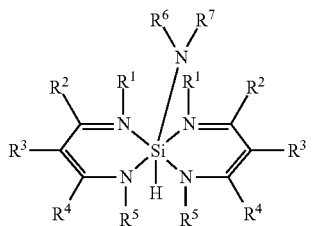

R[1] and R[2] and/or R[2] and R[3] and/or R[3] and R[4] and/or R[4] and R[5] and/or R[6] and R[7] being joined to form cyclic chains;

the compound being:

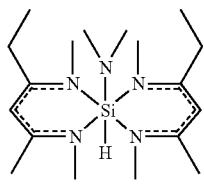

the compound being:

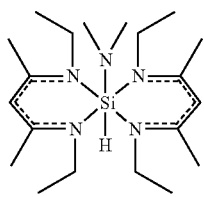

the compound being:

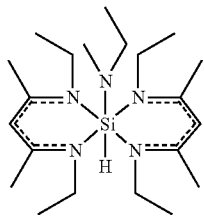

the compound being:

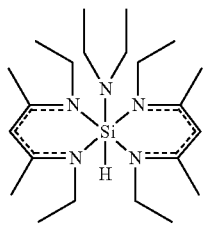

the compound being:

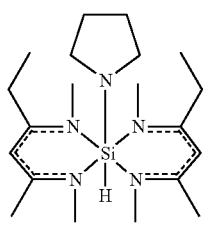

the compound being:

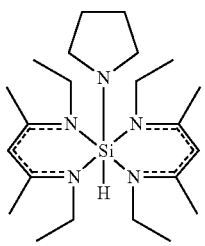

the compound being:

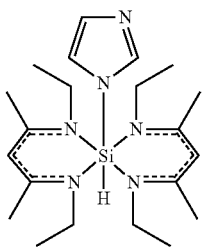

the compound being:

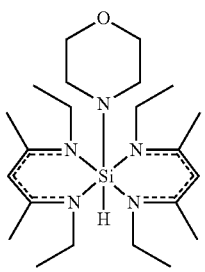

x=0;
z=2;
the compound having the formula:

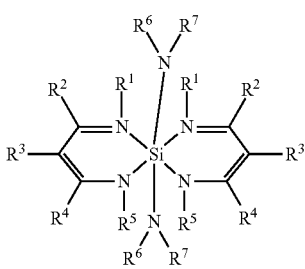

R[1] and R[2] and/or R[2] and R[3] and/or R[3] and R[4] and/or R[4] and R[5] and/or R[6] and R[7] being joined to form cyclic chains;

the compound being:

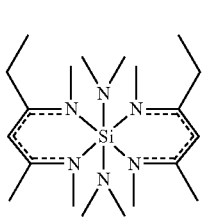

the compound being:

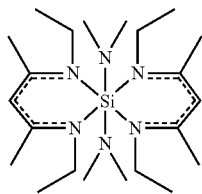

the compound being:

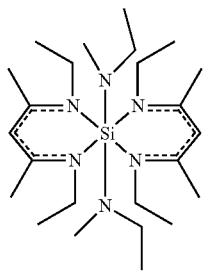

the compound being:

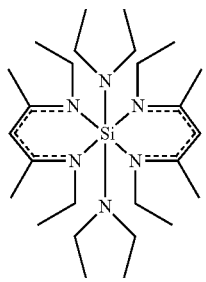

the compound being:

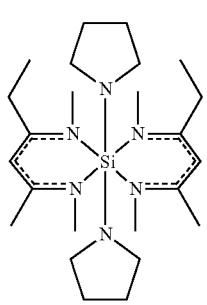

the compound being:

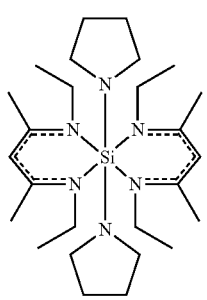

the compound being:

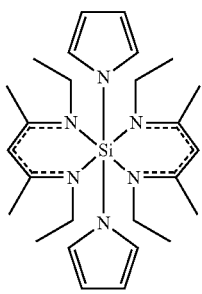

the compound being:

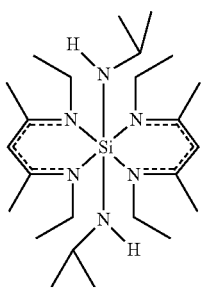

the compound being:

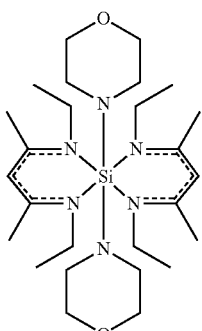

the compound being:

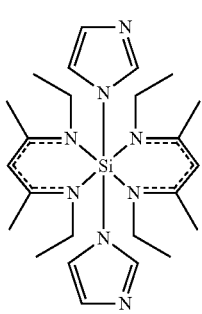

the organosilane precursor composition comprising between approximately 95% w/w and approximately 100% w/w of the compound;

the organosilane precursor composition comprising between approximately 5% w/w and approximately 50% w/w of the compound;

the organosilane precursor composition comprising between approximately 0 ppbw and approximately 100 ppbw Al;
the organosilane precursor composition comprising between approximately 0 ppbw and approximately 100 ppbw As;
the organosilane precursor composition comprising between approximately 0 ppbw and approximately 100 ppbw Ba;
the organosilane precursor composition comprising between approximately 0 ppbw and approximately 100 ppbw Be;
the organosilane precursor composition comprising between approximately 0 ppbw and approximately 100 ppbw Bi;
the organosilane precursor composition comprising between approximately 0 ppbw and approximately 100 ppbw Cd;
the organosilane precursor composition comprising between approximately 0 ppbw and approximately 100 ppbw Ca;
the organosilane precursor composition comprising between approximately 0 ppbw and approximately 100 ppbw Cr;
the organosilane precursor composition comprising between approximately 0 ppbw and approximately 100 ppbw Co;
the organosilane precursor composition comprising between approximately 0 ppbw and approximately 100 ppbw Cu;
the organosilane precursor composition comprising between approximately 0 ppbw and approximately 100 ppbw Ga;
the organosilane precursor composition comprising between approximately 0 ppbw and approximately 100 ppbw Ge;
the organosilane precursor composition comprising between approximately 0 ppbw and approximately 100 ppbw Hf;
the organosilane precursor composition comprising between approximately 0 ppbw and approximately 100 ppbw Zr;
the organosilane precursor composition comprising between approximately 0 ppbw and approximately 100 ppbw In;
the organosilane precursor composition comprising between approximately 0 ppbw and approximately 100 ppbw Fe;
the organosilane precursor composition comprising between approximately 0 ppbw and approximately 100 ppbw Pb;
the organosilane precursor composition comprising between approximately 0 ppbw and approximately 100 ppbw Li;
the organosilane precursor composition comprising between approximately 0 ppbw and approximately 100 ppbw Mg;
the organosilane precursor composition comprising between approximately 0 ppbw and approximately 100 ppbw Mn;
the organosilane precursor composition comprising between approximately 0 ppbw and approximately 100 ppbw W;
the organosilane precursor composition comprising between approximately 0 ppbw and approximately 100 ppbw Ni;
the organosilane precursor composition comprising between approximately 0 ppbw and approximately 100 ppbw K;
the organosilane precursor composition comprising between approximately 0 ppbw and approximately 100 ppbw Na;
the organosilane precursor composition comprising between approximately 0 ppbw and approximately 100 ppbw Sr;
the organosilane precursor composition comprising between approximately 0 ppbw and approximately 100 ppbw Th;
the organosilane precursor composition comprising between approximately 0 ppbw and approximately 100 ppbw Sn;
the organosilane precursor composition comprising between approximately 0 ppbw and approximately 100 ppbw Ti;
the organosilane precursor composition comprising between approximately 0 ppbw and approximately 100 ppbw U;
the organosilane precursor composition comprising between approximately 0 ppbw and approximately 100 ppbw V;
the organosilane precursor composition comprising between approximately 0 ppbw and approximately 100 ppbw Zn;
the organosilane precursor composition comprising between approximately 0 ppmw and approximately 100 ppmw Cl;
the organosilane precursor composition comprising between approximately 0 ppmw and approximately 100 ppmw Br; and
the organosilane precursor composition comprising between approximately 0 ppmw and approximately 100 ppmw I.

Also disclosed are methods of depositing a Si-containing layer on a substrate. An organosilane precursor disclosed above is introduced into a reactor having a substrate disposed therein. At least part of the organosilane precursor is deposited onto the substrate to form a Si-containing layer using a vapor deposition method. The disclosed methods may have one or more of the following aspects:

Introducing into the reactor a vapor comprising a second precursor;
an element of the second precursor being selected from the group consisting of group 2, group 13, group 14, transition metal, lanthanides, and combinations thereof;
the element of the second precursor being selected from Mg, Ca, Sr, Ba, Zr, Hf, Ti, Nb, Ta, Al, Si, Ge, Y, or lanthanides;
Introducing a reactant into the reactor;
the reactant being selected from the group consisting of $O_2$, $O_3$, $H_2O$, $H_2O_2$, NO, $NO_2$, a carboxylic acid, radicals thereof, and combinations thereof;
the reactant being plasma treated oxygen;
the reactant being ozone;
the Si-containing layer being a silicon oxide layer;
the reactant being selected from the group consisting of $H_2$, $NH_3$, $(SiH_3)_3N$, hydridosilanes (such as $SiH_4$, $Si_2H_6$, $Si_3H_8$, $Si_4H_{10}$, $Si_5H_{10}$, $Si_6H_{12}$), chlorosilanes and chloropolysilanes (such as $SiHCl_3$, $SiH_2Cl_2$, $SiH_3Cl$, $Si_2Cl_6$, $Si_2HCl_5$, $Si_3Cl_8$), alkysilanes (such as $Me_2SiH_2$, $Et_2SiH_2$, $MeSiH_3$, $EtSiH_3$), hydrazines (such as $N_2H_4$, $MeHNNH_2$, MeHNNHMe), organic amines (such as $NMeH_2$, $NEtH_2$, $NMe_2H$, $NEt_2H$, $NMe_3$, $NEt_3$, $(SiMe_3)_2NH$), pyrazoline, pyridine, B-containing molecules (such as $B_2H_6$, 9-borabicylo[3,3,1]none, trimethylboron, triethylboron, borazine), alkyl metals (such as trimethylaluminum, triethylaluminum, dimethylzinc, diethylzinc), radical species thereof, and mixtures thereof;

the reactant being selected from the group consisting of $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, and mixtures thereof;

the reactant being HCDS or PCDS;

the vapor deposition method being a chemical vapor deposition process;

the vapor deposition method being an ALD process;

the vapor deposition method being a spatial ALD process;

the silicon-containing layer being Si;

the silicon-containing layer being $SiO_2$;

the silicon-containing layer being SiN;

the silicon-containing layer being SiON;

the silicon-containing layer being SiCN; and the silicon-containing layer being SiCOH.

Notation and Nomenclature

The following detailed description and claims utilize a number of abbreviations, symbols, and terms, which are generally well known in the art. While definitions are typically provided with the first instance of each acronym, for convenience, Table 1 provides a list of the abbreviations, symbols, and terms used along with their respective definitions.

TABLE 1

| a or an | One or more than one |
|---|---|
| Approximately or about | ±10% of the value stated |
| CVD | chemical vapor deposition |
| LCD-TFT | liquid-crystal display |
| TFT | thin-film transistor |
| ALD | atomic layer deposition |
| spatial ALD | spatial atomic layer deposition |
| LPCVD | low pressure chemical vapor deposition |
| P-CVD | pulsed chemical vapor deposition |
| PE-CVD | plasma enhanced chemical vapor deposition |
| PE-ALD | plasma enhanced atomic layer deposition |
| MOCVD | metal organic chemical vapor deposition |
| Flowable PECVD | flowable plasma enhanced chemical vapor deposition |
| sccm | standard cubic centimeters per minute |
| MIM | Metal-insulator-metal |
| DRAM | dynamic random-access memory |
| FeRam | Ferroelectric random-access memory |
| SRO | strontium ruthenium oxide |
| HCDS | Hexachlorodisilane |
| PCDS | Pentachlorodisilane |
| LAH | lithium aluminum hydride |
| TriDMAS or TDMAS | Tris(dimethylamino)silane or $SiH(NMe_2)_3$ |
| BDMAS | Bis(dimethylamino)silane or $SiH_2(NMe_2)_2$ |
| BDEAS | Bis(diethylamino)silane or $SiH_2(NEt_2)_2$ |
| TDEAS | Tris(diethylamino)silane or $SiH(NEt_2)_3$ |
| TEMAS | Tris(ethylmethylamino)silane or $SiH(NEtMe)_3$ |
| TMA | trimethyl aluminum or $AlMe_3$ |
| TBTDET | (tert-butylimido)tris(diethylamido) tantalum or $Ta(=NtBu)(NEt_2)_3$ |
| TAT-DMAE | tantalum tetraethoxide dimethylaminoethoxide or $Ta(OEt)_4(OCH_2CH_2NMe_2)$ |
| PET | polyethylene terephthalate |
| TBTDEN | (tert-butylimido)bis(dimethylamino)niobium or $Nb(=NtBu)(NMe_2)_2$ |
| PEN | polyethylene naphthalate |
| $Ln(tmhd)_3$ | lanthanide (2,2,6,6-tetramethyl-3,5-heptanedione)$_3$ |
| Alkyl group | saturated functional groups containing exclusively carbon and hydrogen atoms, including linear, branched, or cyclic alkyl groups |

TABLE 1-continued

| Me | Methyl |
|---|---|
| Et | Ethyl |
| Pr | Propyl |
| iPr | Isopropyl |
| nPr | n-propyl |
| Bu | Butyl |
| tBu | tert-butyl |
| sBu | sec-butyl |
| iBu | iso-butyl |
| nBu | n-butyl |
| Ph | phenyl |
| Am | Amyl or pentyl |
| tAm | tAmyl or 1,1-dimethylpropyl |
| Cy | cyclic alkyl group |
| R-amd | R—N—C(Me)—N—R amidinate ligand with R being an alkyl group |
| aryl | aromatic ring compounds where one hydrogen atom has been removed from the ring |
| heterocycle | cyclic compounds that has atoms of at least two different elements as members of its ring |

The standard abbreviations of the elements from the periodic table of elements are used herein. It should be understood that elements may be referred to by these abbreviations (e.g., Si refers to silicon, N refers to nitrogen, O refers to oxygen, C refers to carbon, etc.).

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x(NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

DESCRIPTION OF PREFERRED EMBODIMENTS

Disclosed are organosilane precursor compositions comprising compounds having the following formula:

$$SiH_x(RN\!-\!(CR)_n\!-\!NR)_y(NRR)_z \qquad (I)$$

wherein R may each independently be H, a $C_1$ to $C_6$ alkyl group, or a $C_3$-$C_{20}$ aryl or heterocycle group, n, x, y and z are integers and x+y+z=4, provided that x≠3 when y=1. Preferably, n=1 or 3, x=0 to 2, y=1 to 2, and z=1 to 3.

As illustrated below, the disclosed compounds may have a pentacoordinate or hexacoordinate silicon (+IV) center.

When y=1 in the formula (I), the RN—$(CR)_n$—NR ligand bonds to the silicon atom via its two N atoms, resulting in a precursor with a pentacoordinate Si(IV) center. The (RN—$(CR)_n$—NR) ligand forms a ring structure with the silicon via one or three CR(s) (n=1 or 3). The carbon atom(s) in the backbone of the bidentate monoanionic ligand may be sp$^2$ hybridized, resulting in a delocalized charge across the ligand. The carbon atoms may independently be substituted by H, $C_1$-$C_6$ alkyl groups, or $C_3$-$C_{20}$ aryl or heterocycle groups.

When y=2 in the formula (I), each of the two (RN—$(CR)_n$—NR) ligands bond to the silicon atom via the two N atoms, resulting in a precursor with a hexacoordinate Si(IV) center. The hexacoordinate organosilane compounds contain two ring structures, each formed by the bonds between the two nitrogens of the (RN—$(CR)_n$—NR) ligand with the silicon atom. The carbon atoms in the (RN—$(CR)_n$—NR)

ligands may be sp² hybridized, resulting in a delocalized charge across the monoanionic ligand. Alternatively, the carbon atoms in the (RN—(CR)$_n$—NR) ligands may be sp³ hybridized or some combination of sp² and sp³ hybridized, resulting in a negative charge on one of nitrogens in each ring structure and a neutral charge on the other nitrogen in the same ring structure. Each of the nitrogen and carbon atoms may independently be substituted by H, $C_1$-$C_6$ alkyl groups, or $C_3$-$C_{20}$ aryl or heterocycle groups.

Preferably, the disclosed organosilane compounds have suitable properties for vapor depositions methods, such as high vapor pressure, low melting point (preferably being in liquid form at room temperature), low sublimation point, and high thermal stability.

The disclosed organosilane precursors may be suitable for the deposition of Si-containing films by various ALD or CVD processes and may have the following advantages:
- liquid at room temperature or having a melting point lower than 50° C.;
- thermally stable to enable proper distribution (gas phase or direct liquid injection) without particles generation;
- suitable reactivity with the substrate to permit a wide self-limited ALD window, allowing deposition of a variety of Si-, Ge- and Sn-containing films, including ternary or quaternary materials, by using one or a combination of reactants (selected from the group comprising of $H_2$, $NH_3$, $O_2$, $H_2O$, $O_3$, $SiH_4$, $Si_2H_6$, $Si_3H_8$, $SiH(NMe_2)_3$(TriDMAS or TDMAS), $SiH_2(NMe_2)_2$(BDMAS), $SiH_2(N(Et)_2)_2$(BDEAS), $SiH(N(Et)_2)_3$(TDEAS), $SiH(NEtMe)_3$ (TEMAS), $(SiH_3)_3N$, $(SiH_3)_2O$, an aluminum-containing precursor such as trimethyl aluminum (TMA), (tert-butylimido)tris(diethylamido) tantalum (TBTDET), tantalum tetraethoxide dimethylaminoethoxide (TAT-DMAE), polyethylene terephthalate (PET), (tert-butylimido)bis(dimethylamino)niobium (TBTDEN), polyethylene naphthalate (PEN), lanthanide-containing precursors such as $Ln(tmhd)_3$ (lanthanide (2,2,6,6-tetramethyl-3,5-heptanedione)$_3$)).

When n=1, x=2, y=1 and z=1 in formula (I), exemplary organosilane precursors include $H_2Si[RN(CR)NR](NRR)$, and each precursor molecule contains amidinate, amido and hydride functional groups, have the structural formula:

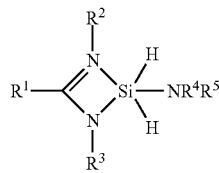

wherein $R^1$, $R^2$, $R^3$, $R^4$ and $R^5$ may each independently be H, a $C_1$ to $C_6$ alkyl group, or a $C_3$-$C_{20}$ aryl or heterocycle group, and $R^1$ and $R^2$ and/or $R^1$ and $R^3$ and/or $R^4$ and $R^5$ being joined to form cyclic chains.

Exemplary amino(amidinate)silanes having the formula $H_2Si[RN(CR)NR](NRR)$ include:

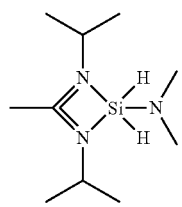 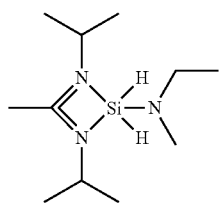

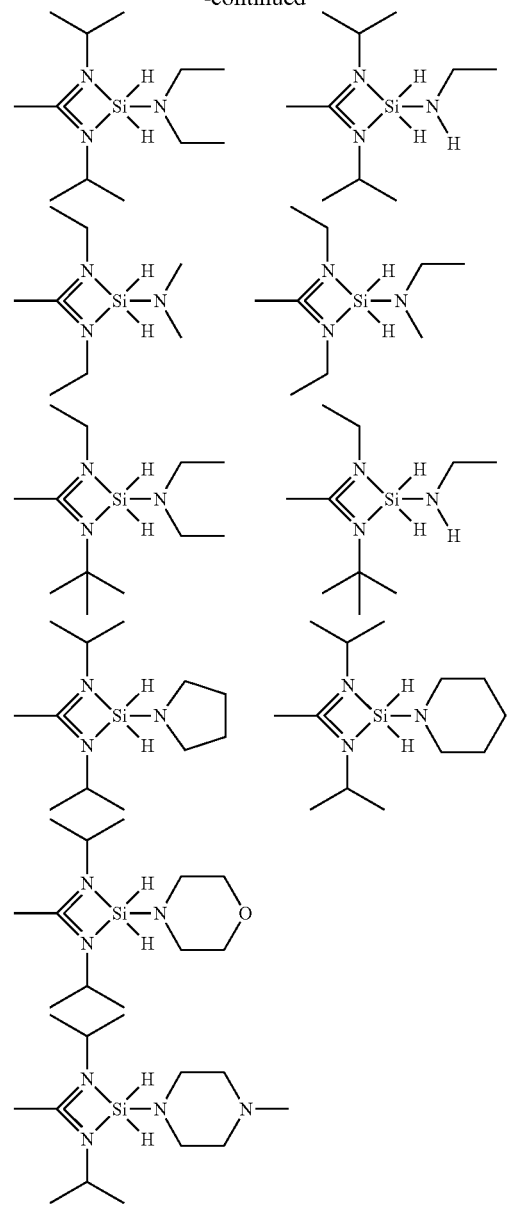

The $H_2Si[RN(CR)NR](NRR)$ precursors may be synthesized by combining a hydrocarbon solution of $SiX_2H_2$, wherein X is Cl, Br, I, or triflate ($SO_3CF_3$), with a neat or hydrocarbon solution of the first ligand compound, such as Li[RN(CR)NR] or Li[NRR] followed by addition of a neat or hydrocarbon solution of the second ligand compound, such as Li[RN(CR)NR] or Li[NRR] under atmosphere of nitrogen, the outlet of the mixing flask being connected to an oil bubbler to inhibit backflow of air and moisture. A second synthetic route to the disclosed $H_2Si[RN(CR)NR](NRR)$ precursors is by combining a hydrocarbon solution of $SiX_2H_2$, wherein X is Cl, Br, I, or triflate ($SO_3CF_3$), with a neat or hydrocarbon solution of the protonated first ligand (HRN(CR)NR or HNRR) followed by a neat or hydrocarbon solution of the protonated second ligand (HRN(CR)NR or HNRR), performed under an inert atmosphere. Alternatively, the disclosed $H_2Si[RN(CR)NR](NRR)$ precursors may be synthesized by reaction of $SiH_nC_{4-n}$ wherein n=0 or 1, with sequentially one equivalent each of the first and second ligand compounds (Li[RN(CR)NR] or Li[NRR]) followed by subsequent reduction using a selected metal hydride such as lithium aluminum hydride (LAH). In all three synthesis routes, the resulting solution may be stirred at room temperature overnight.

Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li[RN(CR)NR] or Li[NRR] all of the starting materials are commercially available. The ligand compound may be synthesized by combining a hydrocarbon solution of metalorganic salt (i.e., alkyl lithium) to a hydrocarbon solution of the appropriate amine or amidine.

When n=1, x=1, y=1 and z=2 in formula (I), exemplary organosilane precursors include HSi[RN(CR)NR](NRR)$_2$, and have the structural formula:

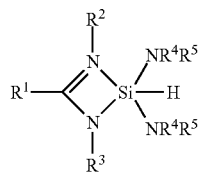

wherein $R^1$, $R^2$, $R^3$, $R^4$ and $R^5$ may each independently be H, a $C_1$ to $C_6$ alkyl group, or a $C_3$-$C_{20}$ aryl or heterocycle group, and $R^1$ and $R^2$ and/or $R^1$ and $R^3$ and/or $R^4$ and $R^5$ being joined to form cyclic chains.

Exemplary amino(amidinate)silanes having the formula HSi[RN(CR)NR](NRR)$_2$ include:

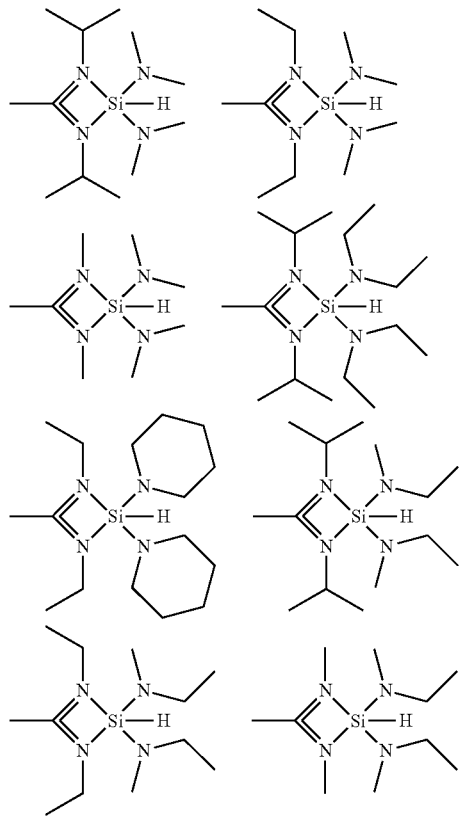

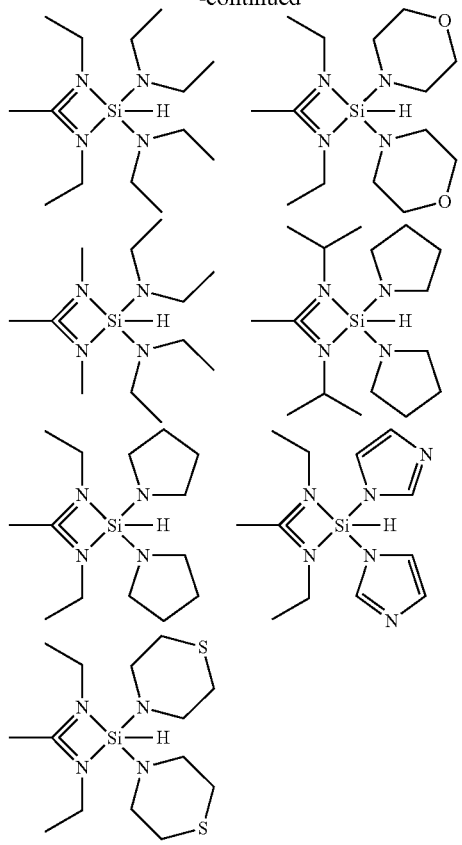

The HSi[RN(CR)NR](NRR)$_2$ precursors may be synthesized by combining a hydrocarbon solution of SiX$_3$H, wherein X is Cl, Br, I, or triflate (SO$_3$CF$_3$), with a neat or hydrocarbon solution of the first ligand compound, such as Li[RN(CR)NR] or Li[NRR] followed by addition of a neat or hydrocarbon solution of the second ligand compound, such as Li[RN(CR)NR] or Li[NRR] under atmosphere of nitrogen, the outlet of the mixing flask being connected to an oil bubbler to inhibit backflow of air and moisture. A second synthetic route to the disclosed HSi[RN(CR)NR](NRR)$_2$ precursors is by combining a hydrocarbon solution of SiX$_3$H, wherein X is Cl, Br, I, or triflate (SO$_3$CF$_3$), with a neat or hydrocarbon solution of the protonated first ligand (HRN(CR)NR or HNRR) followed by a neat or hydrocarbon solution of the protonated second ligand (HRN(CR)NR or HNRR), performed under an inert atmosphere. Alternatively, the disclosed HSi[RN(CR)NR](NRR)$_2$ precursors may be synthesized by reaction of SiCl$_4$ with sequentially one equivalent of the first ligand and two equivalents of the second ligand compounds (Li[RN(CR)NR] or Li[NRR]) followed by subsequent reduction using a selected metal hydride such as LAH. In all three synthesis routes, the resulting solution may be stirred at room temperature overnight.

Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li[RN(CR)NR] or Li[NRR] all of the starting materials are commercially available. The ligand compound may be synthesized by combining a hydrocarbon solution of metalorganic salt (i.e., alkyl lithium) to a hydrocarbon solution of the appropriate amine or amidine.

When n=1, x=0, y=1 and z=3 in formula (I), exemplary organosilane precursors include Si[RN(CR)NR](NRR)$_3$, and have the structural formula:

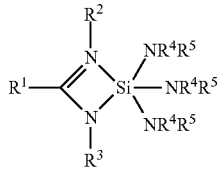

wherein $R^1$, $R^2$, $R^3$, $R^4$ and $R^5$ may each independently be H, a $C_1$ to $C_6$ alkyl group, or a $C_3$-$C_{20}$ aryl or heterocycle group, and $R^1$ and $R^2$ and/or $R^1$ and $R^3$ and/or $R^4$ and $R^5$ being joined to form cyclic chains.

Exemplary tris(amino)amidinatosilanes having the formula Si[RN(CR)NR](NRR)$_3$ include:

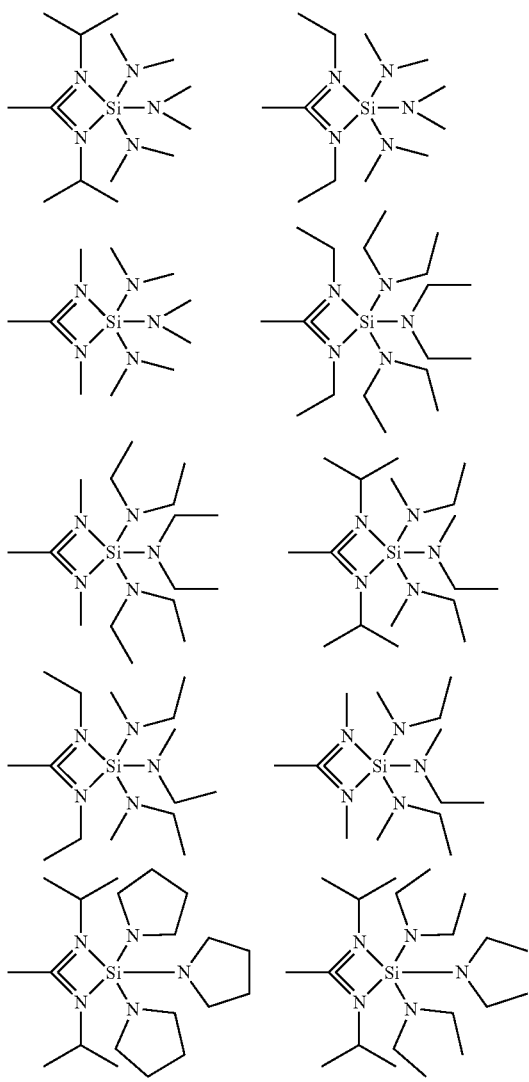

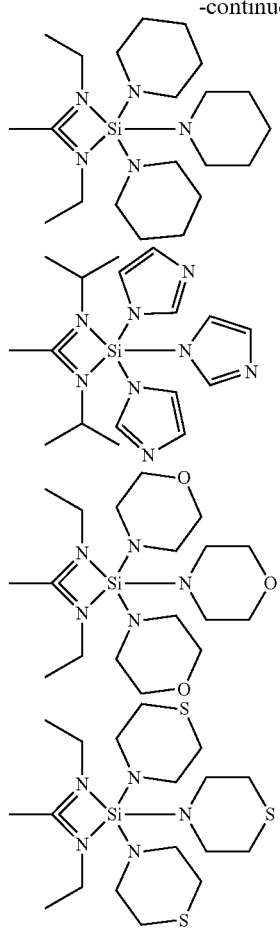

The Si[RN(CR)NR](NRR)$_3$ precursors may be synthesized by combining a hydrocarbon solution of SiX$_4$, wherein X is Cl, Br, I, or triflate (SO$_3$CF$_3$), with a neat or hydrocarbon solution of the first ligand compound, such as Li[RN(CR)NR] or Li[NRR] followed by addition of a neat or hydrocarbon solution of the second ligand compound, such as Li[RN(CR)NR] or Li[NRR] under atmosphere of nitrogen, the outlet of the mixing flask being connected to an oil bubbler to inhibit backflow of air and moisture. A second synthetic route to the disclosed Si[RN(CR)NR](NRR)$_3$ precursors is by combining a hydrocarbon solution of SiX$_4$, wherein X is Cl, Br, I, or triflate (SO$_3$CF$_3$), with a neat or hydrocarbon solution of the protonated first ligand (HRN(CR)NR or HNRR) followed by a neat or hydrocarbon solution of the protonated second ligand (HRN(CR)NR or HNRR), performed under an inert atmosphere.

Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li[RN(CR)NR] or Li[NRR] all of the starting materials are commercially available. The ligand compound may be synthesized by combining a hydrocarbon solution of metalorganic salt (i.e., alkyl lithium) to a hydrocarbon solution of the appropriate amine or amidine.

When n=3, x=2, y=1 and z=1 in the formula (I), exemplary organosilane precursor include H$_2$Si[RN(CR)$_3$NR](NRR), and have the structural formula:

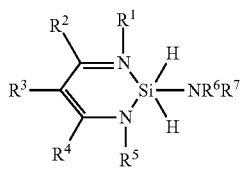

wherein $R^1$, $R^2$, $R^3$, $R^4$, $R^5$, $R^6$ and $R^7$ may each independently be H, a $C_1$ to $C_6$ alkyl group, or a $C_3$-$C_{20}$ aryl or heterocycle group, and $R^1$ and $R^2$ and/or $R^2$ and $R^3$ and/or $R^3$ and $R^4$ and/or $R^4$ and $R^5$ and/or $R^6$ and $R^7$ being joined to form cyclic chains.

Exemplary amino(f-diketiminato)silanes having the formula $HSi[RN(CR)_3NR](NRR)_2$ include:

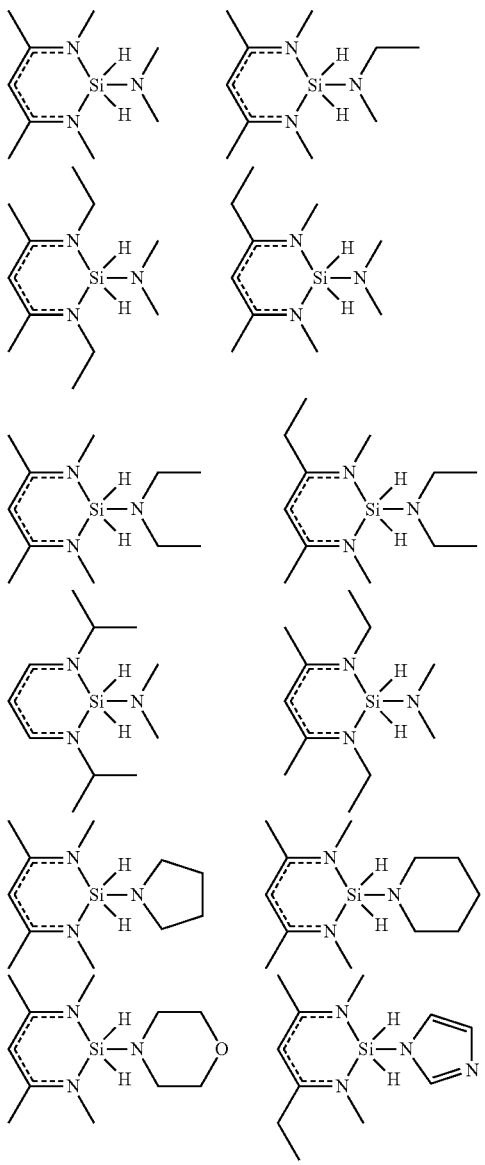

The $H_2Si[RN(CR)_3NR](NRR)$ precursors may be synthesized by combining a hydrocarbon solution of $SiX_2H_2$, wherein X is Cl, Br, I, or triflate ($SO_3CF_3$), with a neat or hydrocarbon solution of the first ligand compound, such as Li[RN(CR)$_3$NR] or Li[NRR] followed by addition of a neat or hydrocarbon solution of the second ligand compound, such as Li[RN(CR)$_3$NR] or Li[NRR] under atmosphere of nitrogen, the outlet of the mixing flask being connected to an oil bubbler to inhibit backflow of air and moisture. A second synthetic route to the disclosed $H_2Si[RN(CR)SNR](NRR)$ precursors is by combining a hydrocarbon solution of $SiX_2H_2$, wherein X is Cl, Br, I, or triflate ($SO_3CF_3$), with a neat or hydrocarbon solution of the protonated first ligand (HRN(CR)$_3$NR or HNRR) followed by a neat or hydrocarbon solution of the protonated second ligand (HRN(CR)$_3$NR or HNRR), performed under an inert atmosphere. Alternatively, the disclosed $H_2Si[RN(CR)_3NR](NRR)$ precursors may be synthesized by reaction of $SiH_nCl_{4-n}$ wherein n=0 or 1, with sequentially one equivalent each of the first and second ligand compounds (Li[RN(CR)$_3$NR] or Li[NRR]) followed by subsequent reduction using a selected metal hydride such as LAH. In all three synthesis routes, the resulting solution may be stirred at room temperature overnight.

Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li[RN(CR)$_3$NR] or Li[NRR] all of the starting materials are commercially available. The ligand compound may be synthesized by combining a hydrocarbon solution of metalorganic salt (i.e., alkyl lithium) to a hydrocarbon solution of the appropriate amine or β-diketimine.

When n=3, x=1, y=1 and z=2 in formula (I), exemplary organosilane precursors include $HSi[RN(CR)_3NR](NRR)_2$, and have the structural formula:

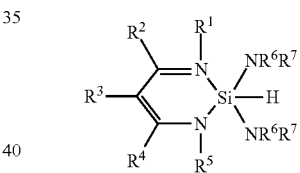

wherein $R^1$, $R^2$, $R^3$, $R^4$, $R^5$, $R^6$ and $R^7$ may each independently be H, a $C_1$ to $C_6$ alkyl group, or a $C_3$-$C_{20}$ aryl or heterocycle group, and $R^1$ and $R^2$ and/or $R^2$ and $R^3$ and/or $R^3$ and $R^4$ and/or $R^4$ and $R^5$ and/or $R^6$ and $R^7$ being joined to form cyclic chains.

Exemplary diamino(β-diketiminato)silanes having the formula $HSi[RN(CR)_3NR](NRR)_2$ include:

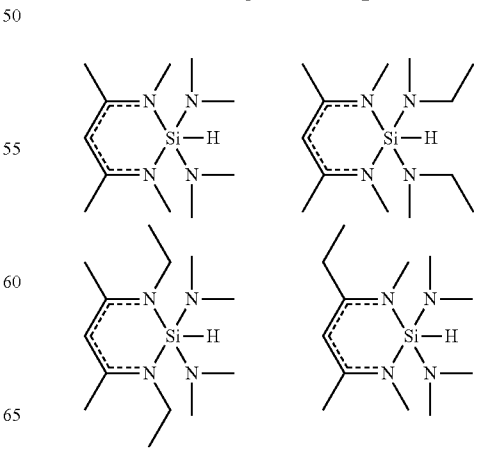

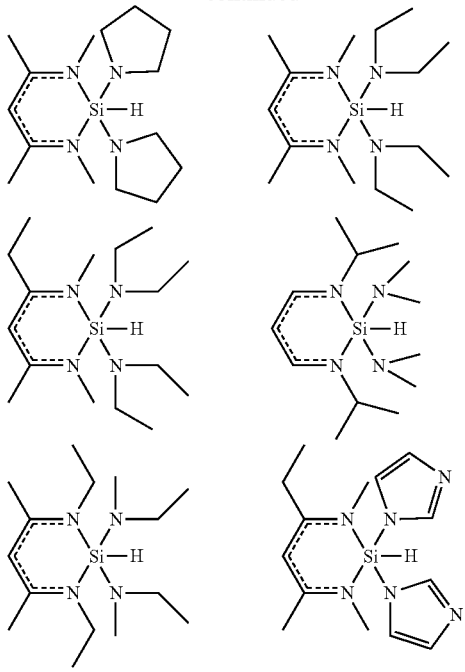

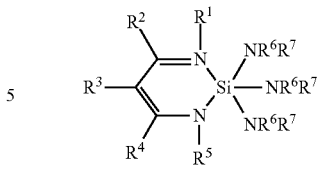

wherein $R^1$, $R^2$, $R^3$, $R^4$, $R^5$, $R^6$ and $R^7$ may each independently be H, a $C_1$ to $C_6$ alkyl group, or a $C_3$-$C_{20}$ aryl or heterocycle group, and $R^1$ and $R^2$ and/or $R^2$ and $R^3$ and/or $R^3$ and $R^4$ and/or $R^4$ and $R^5$ and/or $R^6$ and $R^7$ being joined to form cyclic chains.

Exemplary triamino(β-diketiminato)silanes having the formula Si[RN(CR)₃NR](NRR)₃ include:

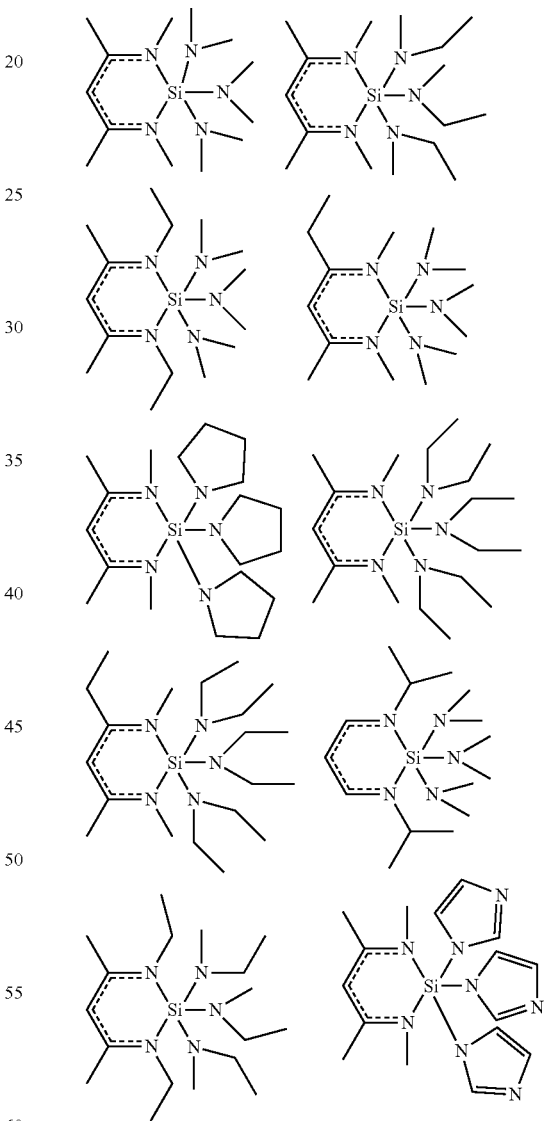

The HSi[RN(CR)₃NR](NRR)₂ precursors may be synthesized by combining a hydrocarbon solution of SiX₃H, wherein X is Cl, Br, I, or triflate (SO₃CF₃), with a neat or hydrocarbon solution of the first ligand compound, such as Li[RN(CR)NR] or Li[NRR] followed by addition of a neat or hydrocarbon solution of the second ligand compound, such as Li[RN(CR)NR] or Li[NRR] under atmosphere of nitrogen, the outlet of the mixing flask being connected to an oil bubbler to inhibit backflow of air and moisture. A second synthetic route to the disclosed HSi[RN(CR)₃NR](NRR)₂ precursors is by combining a hydrocarbon solution of SiX₃H, wherein X is Cl, Br, I, or triflate (SO₃CF₃), with a neat or hydrocarbon solution of the protonated first ligand (HRN(CR)NR or HNRR) followed by a neat or hydrocarbon solution of the protonated second ligand (HRN(CR)NR or HNRR), performed under an inert atmosphere. Alternatively, the disclosed HSi[RN(CR)₃NR](NRR)₂ precursors may be synthesized by reaction of SiCl₄ with sequentially one equivalent of the first ligand and two equivalents of the second ligand compounds (Li[RN(CR)NR] or Li[NRR]) followed by subsequent reduction using a selected metal hydride such as LAH. In all three synthesis routes, the resulting solution may be stirred at room temperature overnight.

Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li[RN(CR)NR] or Li[NRR] all of the starting materials are commercially available. The ligand compound may be synthesized by combining a hydrocarbon solution of metalorganic salt (i.e., alkyl lithium) to a hydrocarbon solution of the appropriate amine or β-diketiminine.

When n=3, x=0, y=1 and z=3 in formula (I), exemplary organosilane precursors include Si[RN(CR)₃NR](NRR)₃, and have the structural formula:

The Si[RN(CR)₃NR](NRR)₃ precursors may be synthesized by combining a hydrocarbon solution of SiX₄, wherein X is Cl, Br, I, or triflate (SO₃CF₃), with a neat or hydrocarbon solution of the first ligand compound, such as Li[RN(CR)₃NR] or Li[NRR] followed by addition of a neat or hydrocarbon solution of the second ligand compound, such as Li[RN(CR)₃NR] or Li[NRR] under atmosphere of nitrogen, the outlet of the mixing flask being connected to an oil bubbler to inhibit backflow of air and moisture. A second synthetic route to the disclosed Si[RN(CR)₃NR](NRR)₃ precursors is by combining a hydrocarbon solution of SiX₄, wherein X is Cl, Br, I, or triflate (SO₃CF₃), with a neat or hydrocarbon solution of the protonated first ligand (HRN(CR)₃NR or HNRR) followed by a neat or hydrocarbon solution of the protonated second ligand (HRN(CR)₃NR or HNRR), performed under an inert atmosphere.

Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li[RN(CR)NR] or Li[NRR] all of the starting materials are commercially available. The ligand compound may be synthesized by combining a hydrocarbon solution of metalorganic salt (i.e., alkyl lithium) to a hydrocarbon solution of the appropriate amine or δ-diketiminine.

When n=1, x=1, y=2 and z=1 in formula (I), exemplary organosilane precursors include HSi[RN(CR)NR]₂(NRR), and have the structural formula:

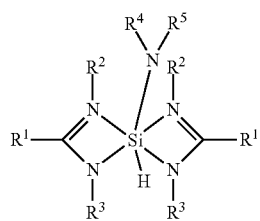

wherein $R^1$, $R^2$, $R^3$, $R^4$ and $R^5$ may each independently be H, a $C_1$ to $C_6$ alkyl group, or a $C_3$-$C_{20}$ aryl or heterocycle group, and $R^1$ and $R^2$ and/or $R^1$ and $R^3$ and/or $R^4$ and $R^5$ being joined to form cyclic chains.

Exemplary bis(amidinato)aminosilanes having the formula HSi[RN(CR)NR]₂(NRR) include:

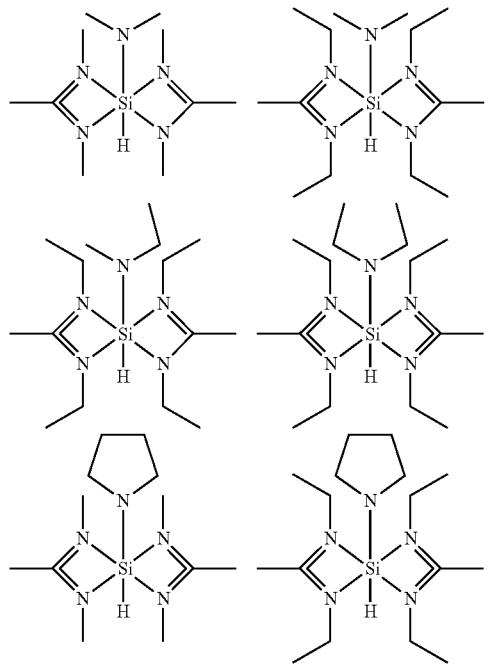

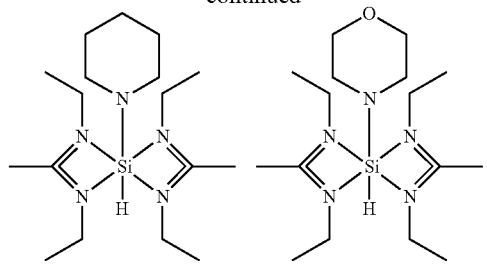

The HSi[RN(CR)NR]₂(NRR) precursors may be synthesized by combining a hydrocarbon solution of SiX₃H, wherein X is Cl, Br, I, or triflate (SO₃CF₃), with a neat or hydrocarbon solution of the first ligand compound, such as Li[RN(CR)NR] or Li[NRR] followed by addition of a neat or hydrocarbon solution of the second ligand compound, such as Li[RN(CR)NR] or Li[NRR] under atmosphere of nitrogen, the outlet of the mixing flask being connected to an oil bubbler to inhibit backflow of air and moisture. A second synthetic route to the disclosed HSi[RN(CR)NR]₂(NRR) precursors is by combining a hydrocarbon solution of SiX₃H, wherein X is Cl, Br, I, or triflate (SO₃CF₃), with a neat or hydrocarbon solution of the protonated first ligand (HRN(CR)NR or HNRR) followed by a neat or hydrocarbon solution of the protonated second ligand (HRN(CR)NR or HNRR), performed under an inert atmosphere. Alternatively, the disclosed HSi[RN(CR)NR]₂(NRR) precursors may be synthesized by reaction of SiCl₄ with sequentially one equivalent of the first ligand and two equivalents of the second ligand compounds (Li[RN(CR)NR] or Li[NRR]) followed by subsequent reduction using a selected metal hydride such as LAH. In all three synthesis routes, the resulting solution may be stirred at room temperature overnight.

Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li[RN(CR)NR] or Li[NRR] all of the starting materials are commercially available. The ligand compound may be synthesized by combining a hydrocarbon solution of metalorganic salt (i.e., alkyl lithium) to a hydrocarbon solution of the appropriate amine or amidine.

When n=1, x=0, y=2 and z=2 in formula (I), exemplary organosilane precursors include Si[RN(CR)NR]₂(NRR)₂, and have the structural formula:

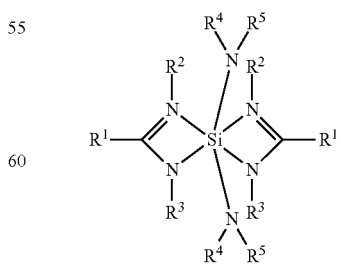

wherein $R^1$, $R^2$, $R^3$, $R^4$ and $R^5$ may each independently be H, a $C_1$ to $C_6$ alkyl group, or a $C_3$-$C_{20}$ aryl or heterocycle group, and $R^1$ and $R^2$ and/or $R^1$ and $R^3$ and/or $R^4$ and $R^5$ being joined to form cyclic chains.

Exemplary bis(amidinato)diaminosilanes having the formula $Si[RN(CR)NR]_2(NRR)_2$ include:

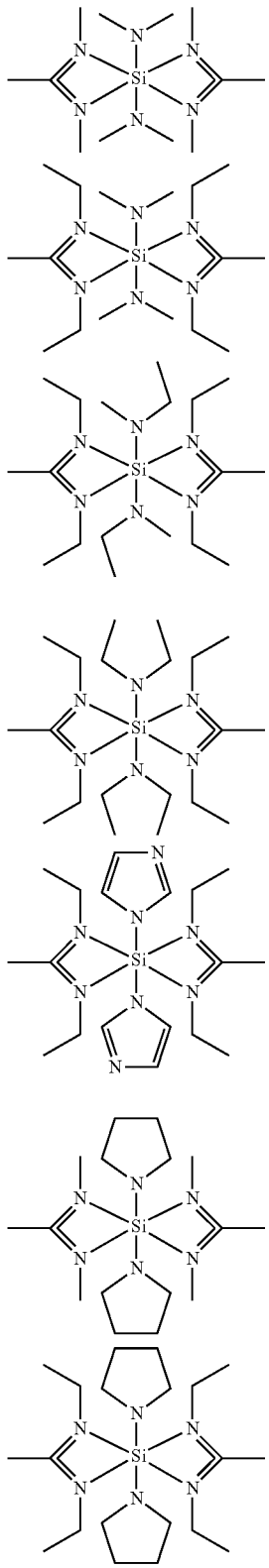

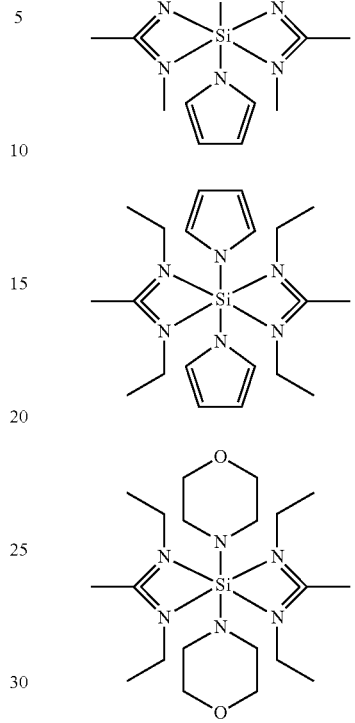

The $Si[RN(CR)NR]_2(NRR)_2$ precursors may be synthesized by combining a hydrocarbon solution of $SiX_4$, wherein X is Cl, Br, I, or triflate ($SO_3CF_3$), with a neat or hydrocarbon solution of the first ligand compound, such as Li[RN(CR)NR] or Li[NRR] followed by addition of a neat or hydrocarbon solution of the second ligand compound, such as Li[RN(CR)NR] or Li[NRR] under atmosphere of nitrogen, the outlet of the mixing flask being connected to an oil bubbler to inhibit backflow of air and moisture. A second synthetic route to the disclosed $Si[RN(CR)NR]_2(NRR)_2$ precursors is by combining a hydrocarbon solution of $SiX_4$, wherein X is Cl, Br, I, or triflate ($SO_3CF_3$), with a neat or hydrocarbon solution of the protonated first ligand (HRN(CR)NR or HNRR) followed by a neat or hydrocarbon solution of the protonated second ligand (HRN(CR)NR or HNRR), performed under an inert atmosphere. In both synthesis routes, the resulting solution may be stirred at room temperature overnight.

Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li[RN(CR)NR] or Li[NRR] all of the starting materials are commercially available. The ligand compound may be synthesized by combining a hydrocarbon solution of metalorganic salt (i.e., alkyl lithium) to a hydrocarbon solution of the appropriate amine or amidine.

When n=3, x=1, y=2 and z=1 in formula (I), exemplary organosilane precursors include $HSi[RN(CR)_3NR]_2(NRR)$, and have the structural formula:

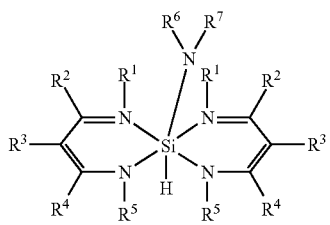

wherein $R^1$, $R^2$, $R^3$, $R^4$, $R^5$, $R^6$ and $R^7$ may each independently be H, a $C_1$ to $C_6$ alkyl group, or a $C_3$-$C_{20}$ aryl or heterocycle group, and $R^1$ and $R^2$ and/or $R^2$ and $R^3$ and/or $R^3$ and $R^4$ and/or $R^4$ and $R^5$ and/or $R^6$ and $R^7$ being joined to form cyclic chains.

Exemplary bis(β-diketiminato)aminosilanes having the formula HSi[RN(CR)$_3$NR]$_2$(NRR) include:

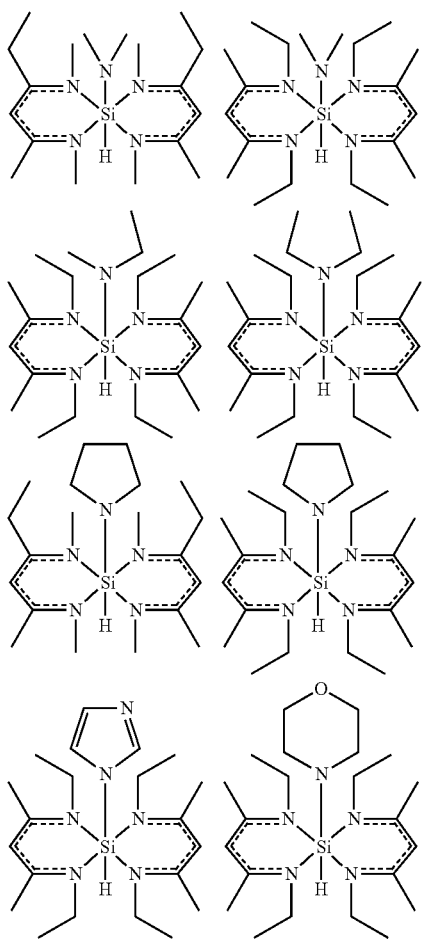

The HSi[RN(CR)$_3$NR]$_2$(NRR) precursors may be synthesized by combining a hydrocarbon solution of SiX$_3$H, wherein X is Cl, Br, I, or triflate (SO$_3$CF$_3$), with a neat or hydrocarbon solution of the first ligand compound, such as Li[RN(CR)NR] or Li[NRR] followed by addition of a neat or hydrocarbon solution of the second ligand compound, such as Li[RN(CR)NR] or Li[NRR] under atmosphere of nitrogen, the outlet of the mixing flask being connected to an oil bubbler to inhibit backflow of air and moisture. A second synthetic route to the disclosed HSi[RN(CR)$_3$NR]$_2$(NRR) precursors is by combining a hydrocarbon solution of SiX$_3$H, wherein X is Cl, Br, I, or triflate (SO$_3$CF$_3$), with a neat or hydrocarbon solution of the protonated first ligand (HRN(CR)NR or HNRR) followed by a neat or hydrocarbon solution of the protonated second ligand (HRN(CR)NR or HNRR), performed under an inert atmosphere. Alternatively, the disclosed HSi[RN(CR)$_3$NR]$_2$(NRR) precursors may be synthesized by reaction of SiCl$_4$ with sequentially one equivalent of the first ligand and two equivalents of the second ligand compounds (Li[RN(CR)NR] or LI[NRR]) followed by subsequent reduction using a selected metal hydride such as LAH. In all three synthesis routes, the resulting solution may be stirred at room temperature overnight.

Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li[RN(CR)NR] or Li[NRR] all of the starting materials are commercially available. The ligand compound may be synthesized by combining a hydrocarbon solution of metalorganic salt (i.e., alkyl lithium) to a hydrocarbon solution of the appropriate amine or β-diketiminine.

When n=3, x=0, y=2 and z=2 in formula (I), exemplary organosilane precursors include Si[RN(CR)$_3$NR]$_2$(NRR)$_2$, and have the structural formula:

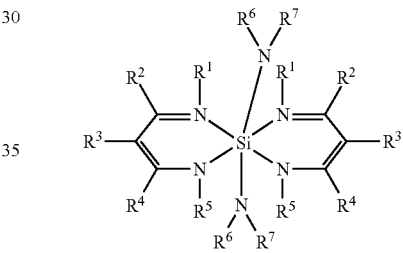

wherein $R^1$, $R^2$, $R^3$, $R^4$, $R^5$, $R^6$ and $R^7$ may each independently be H, a $C_1$ to $C_6$ alkyl group, or a $C_3$-$C_{20}$ aryl or heterocycle group, and $R^1$ and $R^2$ and/or $R^2$ and $R^3$ and/or $R^3$ and $R^4$ and/or $R^4$ and $R^5$ and/or $R^6$ and $R^7$ being joined to form cyclic chains.

Exemplary bis(l-diketiminato)diaminosilanes having the formula Si[RN(CR)$_3$NR]$_2$(NRR)$_2$ include:

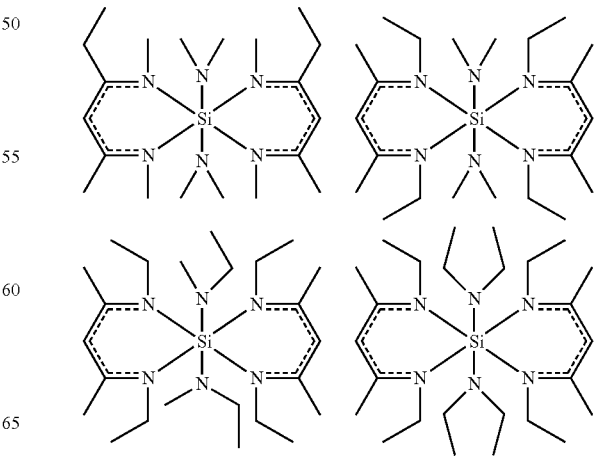

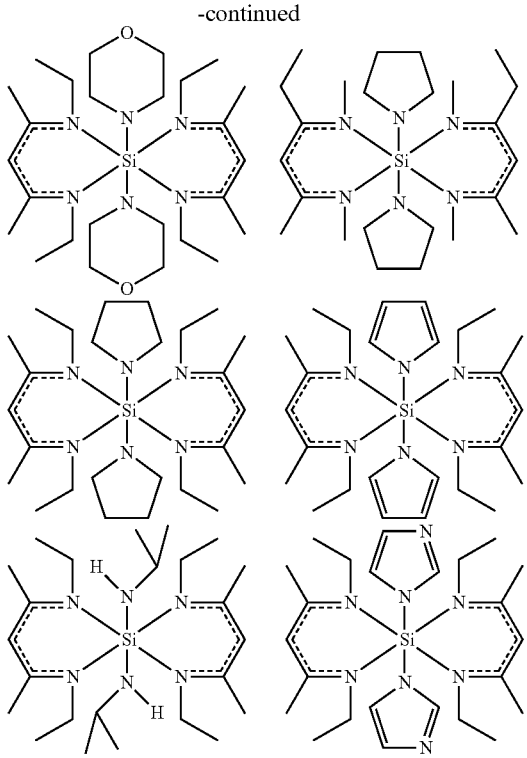

The Si[RN(CR)₃NR]₂(NRR)₂ precursors may be synthesized by combining a hydrocarbon solution of SiX₄, wherein X is Cl, Br, I, or triflate (SO₃CF₃), with a neat or hydrocarbon solution of the first ligand compound, such as Li[RN(CR)NR] or Li[NRR] followed by addition of a neat or hydrocarbon solution of the second ligand compound, such as Li[RN(CR)NR] or Li[NRR] under atmosphere of nitrogen, the outlet of the mixing flask being connected to an oil bubbler to inhibit backflow of air and moisture. A second synthetic route to the disclosed Si[RN(CR)₃NR]₂(NRR)₂ precursors is by combining a hydrocarbon solution of SiX₄, wherein X is Cl, Br, I, or triflate (SO₃CF₃), with a neat or hydrocarbon solution of the protonated first ligand (HRN(CR)₃NR or HNRR) followed by a neat or hydrocarbon solution of the protonated second ligand (HRN(CR)₃NR or HNRR), performed under an inert atmosphere. In both synthesis routes, the resulting solution may be stirred at room temperature overnight.

Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li[RN(CR)₃NR] or Li[NRR] all of the starting materials are commercially available. The ligand compound may be synthesized by combining a hydrocarbon solution of metalorganic salt (i.e., alkyl lithium) to a hydrocarbon solution of the appropriate amine or β-diketiminine.

To ensure process reliability, the disclosed organosilane precursor composition may be purified by continuous or fractional batch distillation prior to use to a purity ranging from approximately 95% w/w to approximately 100% w/w, preferably ranging from approximately 98% w/w to approximately 100% w/w. One of ordinary skill in the art will recognize that the purity may be determined by H NMR or gas or liquid chromatography with mass spectrometry. The organosilane precursor composition may contain any of the following impurities: carbodiimides, alkylamines, dialkylamines, alkylimines, cyclopentadiene, dicyclopentadiene, THF, ether, pentane, cyclohexane, heptanes, toluene, chlorinated metal compounds, lithium, sodium, potassium, lithium amidinate, sodium amidinate, or potassium amidinate. Preferably, the total quantity of these impurities is below 0.1% w/w. The purified composition may be produced by recrystallisation, sublimation, distillation, and/or passing the gas or liquid through a suitable adsorbent, such as a 4 A molecular sieve.

The concentration of each solvent (such as THF, ether, pentane, cyclohexane, heptanes, and/or toluene), in the purified organosilane precursor composition may range from approximately 0% w/w to approximately 5% w/w, preferably from approximately 0% w/w to approximately 0.1% w/w. Solvents may be used in the precursor composition's synthesis. Separation of the solvents from the precursor composition may be difficult if both have similar boiling points. Cooling the mixture may produce solid precursor in liquid solvent, which may be separated by filtration. Vacuum distillation may also be used, provided the precursor composition is not heated above approximately its decomposition point.

The disclosed organosilane precursor composition contains less than 5% v/v, preferably less than 1% v/v, more preferably less than 0.1% v/v, and even more preferably less than 0.01% v/v of any of its mono-, tris-, or tetra-substituted analogs or other reaction products. This embodiment may provide better process repeatability. This embodiment may be produced by distillation of the organosilane precursor composition.

Alternatively, the disclosed organosilane precursor compositions may comprise between approximately 5% w/w to approximately 50% w/w of one compound with the balance of the composition comprising a second compound, particularly when the mixture provides improved process parameters or isolation of the target compound is too difficult or expensive. For example, the disclosed organosilane precursor compositions may be 40/60% w/w of

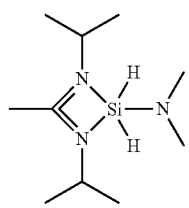

and

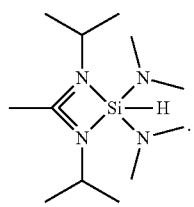

The mixture may produce a stable, liquid composition suitable for vapor deposition.

The concentration of trace metals and metalloids in the purified organosilane precursor composition may each range independently from approximately 0 ppbw to approximately 100 ppbw, and more preferably from approximately 0 ppbw to approximately 10 ppbw. These metal or metalloid impurities include, but are not limited to, Aluminum(Al), Arsenic (As), Barium(Ba), Beryllium(Be), Bismuth(Bi), Cadmium (Cd), Calcium(Ca), Chromium(Cr), Cobalt(Co), Copper (Cu), Gallium(Ga), Germanium(Ge), Hafnium(Hf), Zirconium(Zr), Indium(In), Iron(Fe), Lead(Pb), Lithium (Li), Magnesium(Mg), Manganese(Mn), Tungsten(W), Nickel(Ni), Potassium(K), Sodium(Na), Strontium(Sr), Thorium(Th), Tin(Sn), Titanium(Ti), Uranium(U), Vanadium(V) and Zinc(Zn). The concentration of X (where X=Cl, Br, I) in the purified organosilane precursor composition may range between approximately 0 ppmw and approximately 100 ppmw and more preferably between approximately 0 ppmw to approximately 10 ppmw.

Also disclosed are methods of using the disclosed organosilane precursors for vapor deposition methods. The disclosed methods provide for the use of the organosilane precursors for deposition of silicon-containing films. The disclosed methods may be useful in the manufacture of semiconductor, photovoltaic, LCD-TFT, flat panel type devices, refractory materials, or aeronautics.

The disclosed methods for forming a silicon-containing layer on a substrate include: placing a substrate in a reactor, delivering into the reactor a vapor including the disclosed organosilane precursors, and contacting the vapor with the substrate (and typically directing the vapor to the substrate) to form a silicon-containing layer on the surface of the substrate.

The methods may include forming a bimetal-containing layer on a substrate using the vapor deposition process and, more specifically, for deposition of $SiMO_x$ films wherein x is 4 and M is Ta, Hf, Nb, Mg, Al, Sr, Y, Ba, Ca, As, Sb, Bi, Sn, Pb, Co, lanthanides (such as Er), or combinations thereof. The disclosed methods may be useful in the manufacture of semiconductor, photovoltaic, LCD-TFT, or flat panel type devices. An oxygen source, such as $Os$, $O_2$, $H_2O$, NO, $H_2O_2$, acetic acid, formalin, para-formaldehyde, oxygen radicals thereof, and combinations thereof, but preferably $O_3$ or plasma treated $O_2$, may also be introduced into the reactor.

The disclosed organosilane precursors may be used to deposit silicon-containing films using any deposition methods known to those of skill in the art. Examples of suitable deposition methods include chemical vapor deposition (CVD) or atomic layer deposition (ALD). Exemplary CVD methods include thermal CVD, pulsed CVD (PCVD), low pressure CVD (LPCVD), sub-atmospheric CVD (SACVD) or atmospheric pressure CVD (APCVD), hot-wire CVD (HWCVD, also known as cat-CVD, in which a hot wire serves as an energy source for the deposition process), radicals incorporated CVD, plasma enhanced CVD (PECVD) including but not limited to flowable PECVD, and combinations thereof. Exemplary ALD methods include thermal ALD, plasma enhanced ALD (PEALD), spatial isolation ALD, hot-wire ALD (HWALD), radicals incorporated ALD, and combinations thereof. Super critical fluid deposition may also be used. The deposition method is preferably ALD, PE-ALD, or spatial ALD in order to provide suitable step coverage and film thickness control.

The vapor of the organosilane precursor is generated and then introduced into a reaction chamber containing a substrate. The temperature and the pressure in the reaction chamber and the temperature of the substrate are held at conditions suitable for vapor deposition of at least part of the organosilane precursor onto the substrate. In other words, after introduction of the vaporized precursor into the reaction chamber, conditions within the reaction chamber are adjusted such that at least part of the vaporized precursor is deposited onto the substrate to form the Si-containing layer. One of ordinary skill in the art will recognize that "at least part of the vaporized compound is deposited" means that some or all of the compound reacts with or adheres to the substrate. Herein, a reactant may also be used to help in formation of the Si-containing layer.

The reaction chamber may be any enclosure or chamber of a device in which deposition methods take place, such as, without limitation, a parallel-plate type reactor, a cold-wall type reactor, a hot-wall type reactor, a single-wafer reactor, a multi-wafer reactor, or other such types of deposition systems. All of these exemplary reaction chambers are capable of serving as an ALD or CVD reaction chamber. The reaction chamber may be maintained at a pressure ranging from about 0.5 mTorr to about 20 Torr for all ALD and subatmospheric CVD. Subatmospheric CVD and atmospheric CVD pressures may range up to 760 Torr (atmosphere). In addition, the temperature within the reaction chamber may range from about 20° C. to about 600° C. One of ordinary skill in the art will recognize that the temperature may be optimized through mere experimentation to achieve the desired result.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 20° C. to approximately 600° C. When a plasma deposition process is utilized, the deposition temperature may range from approximately 20° C. to approximately 550° C. Alternatively, when a thermal process is performed, the deposition temperature may range from approximately 300° C. to approximately 600° C.

Alternatively, the substrate may be heated to a sufficient temperature to obtain the desired silicon-containing film at a sufficient growth rate and with desired physical state and composition. A non-limiting exemplary temperature range to which the substrate may be heated includes from 150° C. to 600° C. Preferably, the temperature of the substrate remains less than or equal to 500° C.

The reactor contains one or more substrates onto which the films will be deposited. A substrate is generally defined as the material on which a process is conducted. The substrates may be any suitable substrate used in semiconductor, photovoltaic, flat panel, or LCD-TFT device manufacturing. Examples of suitable substrates include wafers, such as silicon, silica, glass, or GaAs wafers. The wafer may have one or more layers of differing materials deposited on it from a previous manufacturing step. For example, the wafers may include silicon layers (crystalline, amorphous, porous, etc.), silicon oxide layers, silicon nitride layers, silicon oxy nitride layers, carbon doped silicon oxide (SiCOH) layers, or combinations thereof. Additionally, the wafers may include copper layers or noble metal layers (e.g. platinum, palladium, rhodium, or gold). The layers may include oxides which are used as dielectric materials in MIM, DRAM, or FeRam technologies (e.g., $ZrO_2$ based materials, $HfO_2$ based materials, $TiO_2$ based materials, rare earth oxide based materials, ternary oxide based materials such as strontium ruthenium oxide [SRO], etc.) or from nitride-based films (e.g., TaN) that are used as an oxygen barrier between copper and the low-k layer. The wafers may include barrier layers, such as manganese, manganese oxide, etc. Plastic layers, such as poly(3,4-ethylenedioxythiophene)poly(styrenesulfonate) [PEDOT:PSS] may also be used. The layers may be planar or patterned. For example, the layer may be a patterned photoresist film made of hydrogenated carbon, for example $CH_x$, wherein x is greater than zero. The disclosed processes may deposit the silicon-containing layer directly on the wafer or directly on one or more than one (when patterned layers form the substrate) of the layers on top of the wafer. Furthermore, one of ordinary skill in the art will recognize that the terms "film" or "layer" used herein refer to a thickness of some material laid on or spread over a surface and that the surface may be a trench or a line. Throughout the specification and claims, the wafer and any associated layers thereon are referred to as substrates. In many instances though, the preferred substrate utilized may be selected from hydrogenated carbon, TiN, SRO, Ru, and Si type substrates, such as polysilicon or crystalline silicon substrates. For example, a silicon nitride film may be deposited onto a Si layer. In subsequent processing, alternating silicon oxide and silicon nitride layers may be deposited on the silicon nitride layer forming a stack of multiple $SiO_2$/SiN layers used in 3D NAND gates.

The disclosed organosilane precursors may be supplied either in neat form or in a blend with a suitable solvent, such as toluene, ethyl benzene, xylene, mesitylene, decane, dodecane, octane, hexane, pentane, tertiary amines, acetone, tetrahydrofuran, ethanol, ethylmethylketone, 1,4-dioxane, or others. The disclosed precursors may be present in varying concentrations in the solvent. For example, the resulting concentration may range from approximately 0.05M to approximately 2M.

The neat or blended organosilane precursors are delivered into a reactor in vapor form by conventional means, such as tubing and/or flow meters. The precursor in vapor form may be produced by vaporizing the neat or blended precursor solution through a conventional vaporization step such as direct vaporization, distillation, by bubbling, or by using a sublimator such as the one disclosed in PCT Publication WO2009/087609 to Xu et al. The neat or blended precursor may be fed in liquid state to a vaporizer where it is vaporized before it is introduced into the reactor. Alternatively, the neat or blended precursor may be vaporized by passing a carrier gas into a container containing the precursor or by bubbling of the carrier gas into the precursor. The carrier gas may include, but is not limited to, Ar, He, or $N_2$, and mixtures thereof. Bubbling with a carrier gas may also remove any dissolved oxygen present in the neat or blended precursor solution. The carrier gas and precursor are then introduced into the reactor as a vapor.

If necessary, the container may be heated to a temperature that permits the organosilane precursor to be in its liquid phase and to have a sufficient vapor pressure. The container may be maintained at temperatures in the range of, for example, 0-150° C. Those skilled in the art recognize that the temperature of the container may be adjusted in a known manner to control the amount of organosilane precursor vaporized.

In addition to the disclosed precursor, a reactant may also be introduced into the reactor. The reactant may be an oxidizing agent, such as one of $O_2$, $O_3$, $H_2O$, $H_2O_2$; oxygen containing radicals, such as $O^-$ or $OH^-$, NO, $NO_2$; carboxylic acids such as formic acid, acetic acid, propionic acid, radical species of NO, $NO_2$, or the carboxylic acids; paraformaldehyde; and mixtures thereof. Preferably, the oxidizing agent is selected from the group consisting of $O_2$, $O_3$, $H_2O$, $H_2O_2$, oxygen containing radicals thereof such as $O^-$ or $OH^-$, and mixtures thereof. Preferably, when an ALD process is performed, the reactant is plasma treated oxygen, ozone, or combinations thereof. When an oxidizing agent is used, the resulting silicon containing film will also contain oxygen.

Alternatively, the reactant may be a reducing agent such as one of $H_2$, $NH_3$, $(SiH_3)_3N$, hydridosilanes (for example, $SiH_4$, $Si_2H_6$, $Si_3H_8$, $Si_4H_{10}$, $Si_5H_{10}$, $Si_6H_{12}$), chlorosilanes and chloropolysilanes (for example, $SiHCl_3$, $SiH_2Cl_2$, $SIH_3Cl$, $Si_2Cl_6$, $Si_2HCl_5$, $Si_3Cl_8$), alkylsilanes (for example, $(CH_3)_2SiH_2$, $(C_2H_5)_2SiH_2$, $(CH_3)SiH_3$, $(C_2H_5)SiH_3$), hydrazines (for example, $N_2H_4$, $MeHNNH_2$, MeHNNHMe), organic amines (for example, $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$), pyrazoline, pyridine, B-containing molecules (for example, $B_2H_6$, 9-borabicyclo[3,3,1]none, trimethylboron, triethylboron, borazine), alkyl metals (such as trimethylaluminum, triethylaluminum, dimethylzinc, diethylzinc), radical species thereof, and mixtures thereof. Preferably, the reducing agent is $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, or mixtures thereof. Preferably, the reducing agent is $SiHCl_3$, $Si_2Cl_6$, $Si_2HCl_5$, $Si_2H_2Cl_4$, and cyclo-$Si_6H_6Cl_6$. When a reducing agent is used, the resulting silicon containing film may be pure Si.

The reactant may be treated by plasma, in order to decompose the reactant into its radical form. $N_2$ may also be utilized as a reducing agent when treated with plasma. For instance, the plasma may be generated with a power ranging from about 50 W to about 500 W, preferably from about 100 W to about 200 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

The disclosed organosilane precursors may also be used with a halosilane or polyhalodisilane, such as hexachlorodisilane pentachlorodisilane, or tetrachlorodisilane, and one or more reactants to form Si, SiCN, or SiCOH films. PCT Publication Number WO2011/123792 discloses a SiN layer (not a Si or SiCOH layer), and the entire contents of which are incorporated herein in their entireties.

When the desired silicon-containing film also contains another element, such as, for example and without limitation, Ta, Hf, Nb, Mg, Al, Sr, Y, Ba, Ca, As, Sb, Bi, Sn, Pb, Co, lanthanides (such as Er), or combinations thereof, the reactants may include a metal-containing precursor which is selected from, but not limited to, metal alkyls, such as $Ln(RCp)_3$ or $Co(RCp)_2$, metal amines, such as $Nb(Cp)$ $(NtBu)(NMe_2)_3$ and any combination thereof.

The organosilane precursor and one or more reactants may be introduced into the reaction chamber simultaneously (e.g., CVD), sequentially (e.g., ALD), or in other combinations. For example, the organosilane precursor may be introduced in one pulse and two additional metal sources may be introduced together in a separate pulse (e.g., modified ALD). Alternatively, the reaction chamber may already contain the reactant prior to introduction of the organosilane precursor. The reactant may be passed through a plasma system localized or remotely from the reaction chamber, and decomposed to radicals. Alternatively, the organosilane precursor may be introduced to the reaction chamber continuously while other metal sources are introduced by pulse (e.g., pulsed-CVD). In each example, a pulse may be followed by a purge or evacuation step to remove excess amounts of the component introduced. In each example, the pulse may last for a time period ranging from about 0.01 s to about 10 s, alternatively from about 0.3 s to about 3 s, alternatively from about 0.5 s to about 2 s. In another alternative, the organosilane precursor and one or more reactants may be simultaneously sprayed from a shower head under which a susceptor holding several wafers is spun (e.g., spatial ALD).

In one non-limiting exemplary ALD type process, the vapor phase of an organosilane precursor is introduced into the reaction chamber, where it is contacted with a suitable substrate. Excess organosilane precursor may then be removed from the reaction chamber by purging and/or evacuating the reaction chamber. An oxygen source is introduced into the reaction chamber where it reacts with the absorbed organosilane precursor in a self-limiting manner. Any excess oxygen source is removed from the reaction chamber by purging and/or evacuating the reaction chamber. If the desired film is a silicon oxide film, this two-step process may provide the desired film thickness or may be repeated until a film having the necessary thickness has been obtained.

Alternatively, if the desired film is a silicon metal oxide film (i.e., $SiMO_x$, wherein x may be 4 and M is Ta, Hf, Nb, Mg, Al, Sr, Y, Ba, Ca, As, Sb, Bi, Sn, Pb, Co, lanthanides (such as Er), or combinations thereof), the two-step process above may be followed by introduction of a second vapor of a metal-containing precursor into the reaction chamber. The metal-containing precursor will be selected based on the nature of the silicon metal oxide film being deposited. After introduction into the reaction chamber, the metal-containing precursor is contacted with the substrate. Any excess metal-containing precursor is removed from the reaction chamber by purging and/or evacuating the reaction chamber. Once again, an oxygen source may be introduced into the reaction chamber to react with the metal-containing precursor. Excess oxygen source is removed from the reaction chamber by purging and/or evacuating the reaction chamber. If a desired film thickness has been achieved, the process may be terminated. However, if a thicker film is desired, the entire four-step process may be repeated. By alternating the provision of the organosilane precursor, metal-containing precursor, and oxygen source, a film of desired composition and thickness can be deposited.

Additionally, by varying the number of pulses, films having a desired stoichiometric M:Si ratio may be obtained. For example, a $SiMO_2$ film may be obtained by having one pulse of the organosilane precursor and one pulses of the metal-containing precursor, with each pulse being followed by pulses of the oxygen source. However, one of ordinary skill in the art will recognize that the number of pulses required to obtain the desired film may not be identical to the stoichiometric ratio of the resulting film.

In another alternative, dense SiCN films may be deposited using an ALD method with hexachlorodisilane (HCDS) or pentachlorodisilane (PCDS), the disclosed organosilane precursor, and an ammonia reactant. The reaction chamber may be controlled at 5 Torr, 550° C., with a 55 sccm continuous flow of Ar. An approximately 10 second long pulse of the organosilane precursor at a flow rate of approximately 1 sccm is introduced into the reaction chamber. The organosilane precursor is purged from the reaction chamber with an approximately 55 sccm flow of Ar for approximately 30 seconds. An approximately 10 second pulse of HCDS at a flow rate of approximately 1 sccm is introduced into the reaction chamber. The HCDS is purged from the reaction chamber with an approximately 55 sccm flow of Ar for approximately 30 seconds. An approximately 10 second long pulse of $NH_3$ at a flow rate of approximately 50 sccm is introduced into the reaction chamber. The $NH_3$ is purged from the reaction chamber with an approximately 55 sccm flow of Ar for approximately 10 seconds. These 6 steps are repeated until the deposited layer achieves a suitable thickness. One of ordinary skill in the art will recognize that the introductory pulses may be simultaneous when using a spatial ALD device. As described in PCT Pub No WO2011/123792, the order of the introduction of the precursors may be varied and the deposition may be performed with or without the $NH_3$ reactant in order to tune the amounts of carbon and nitrogen in the SiCN film.

In yet another alternative, a silicon-containing film may be deposited by the flowable PECVD method disclosed in U.S. Patent Application Publication No. 2014/0051264 using the disclosed compounds and a radical nitrogen- or oxygen-containing reactant. The radical nitrogen- or oxygen-containing reactant, such as $NH_3$ or $H_2O$ respectively, is generated in a remote plasma system. The radical reactant and the vapor phase of the disclosed precursors are introduced into the reaction chamber where they react and deposit the initially flowable film on the substrate. Applicants believe that the nitrogen atoms of the $(RN-(CR)_n-NR)$ ligand and amino groups in the disclosed compounds help to further improve the flowability of the deposited film, resulting in films having less voids.

The silicon-containing films resulting from the processes discussed above may include $SiO_2$, SiN, SiON, SiCN, SiCOH, or $MSiO_x$, wherein M is an element such as Hf, Zr, Ti, Nb, Ta, or Ge, and x may be from 0-4, depending of course on the oxidation state of M. One of ordinary skill in the art will recognize that by judicial selection of the appropriate organosilane precursor and reactants, the desired film composition may be obtained.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the silicon-containing film may be exposed to a temperature ranging from approximately 200° C. and approximately 1000° C. for a time ranging from approximately 0.1 second to approximately 7200 seconds under an inert atmosphere, a H-containing atmosphere, a N-containing atmosphere, an O-containing atmosphere, or combinations thereof. Most preferably, the temperature is 600° C. for less than 3600 seconds under a H-containing atmosphere. The resulting film may contain fewer impurities and therefore may have improved performance characteristics. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, has been found effective to reduce carbon and nitrogen contamination of the silicon-containing film.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

What is claimed is:

1. A Si-containing film forming composition comprising an organosilane precursor having the formula:

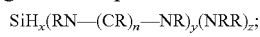

wherein each R is independently selected from the group consisting of H, a $C_1$ to $C_6$ alkyl group, and a $C_3$-$C_{20}$ aryl or heterocycle group; n=1 or 3; x=0, 1, or 2; y=1 or 2; and z=1, 2, or 3; and x+y+z=4, provided that x≠2 when y=2.

2. The Si-containing film forming composition of claim 1, wherein n=1, x=2, y=1, z=1, and the organosilane precursor has the formula:

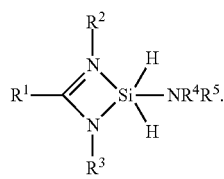

3. The Si-containing film forming composition of claim 2, wherein the organosilane precursor is selected from the group consisting of:

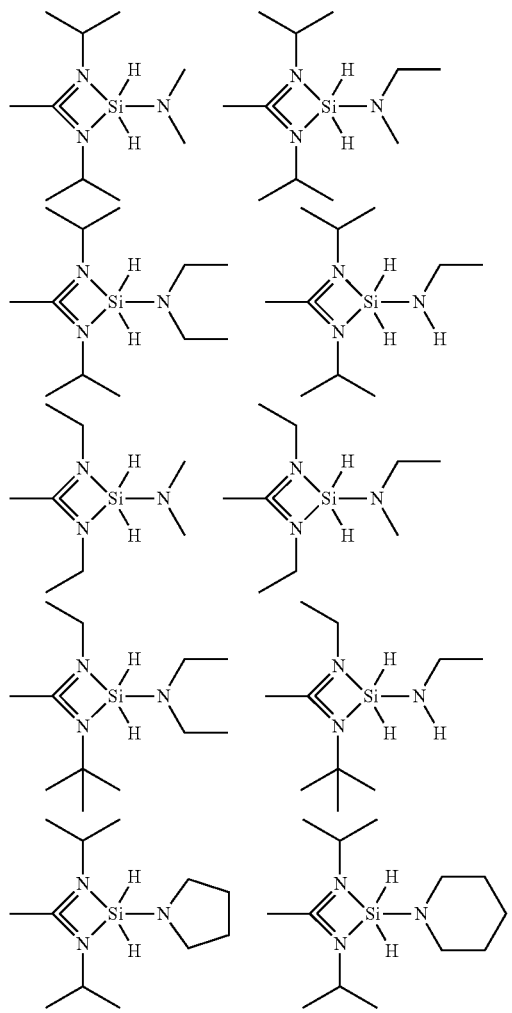

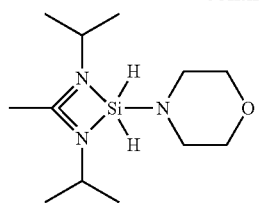

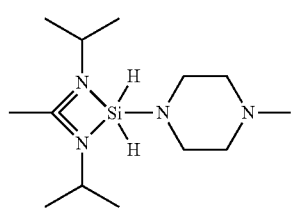

4. The Si-containing film forming composition of claim 3, wherein the organosilane precursor is $SiH_2(NMe_2)(iPr\text{-}amd)$ or $SiH_2(NEt_2)(iPr\text{-}amd)$.

5. The Si-containing film forming composition of claim 1, wherein n=1, x=1, y=1, z=2, and the organosilane precursor has the formula:

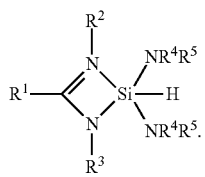

6. The Si-containing film forming composition of claim 5, wherein the organosilane precursor is selected from the group consisting of:

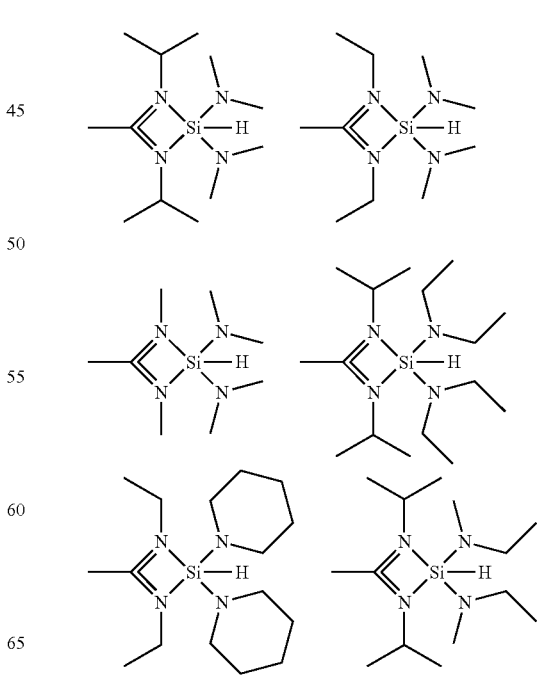

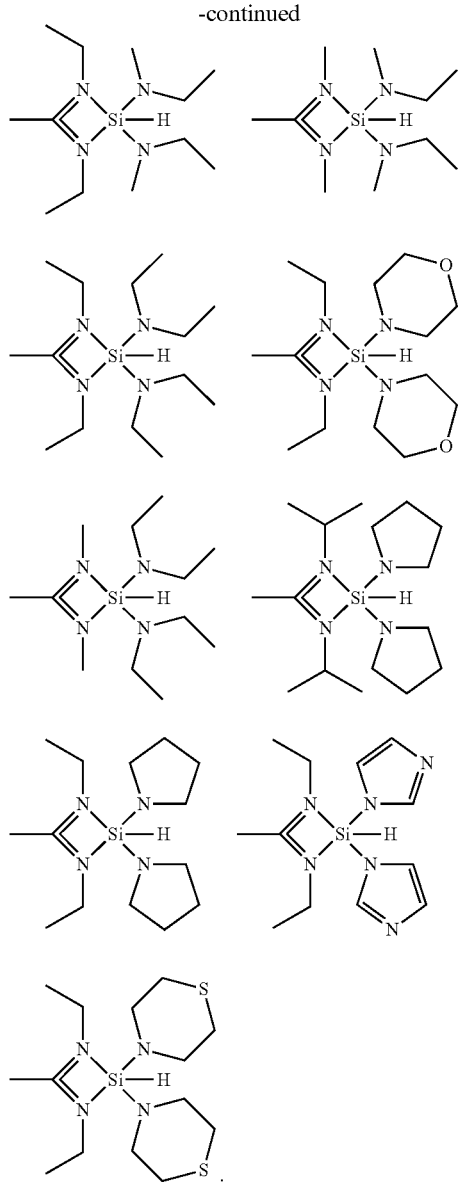

7. The Si-containing film forming composition of claim 6, wherein the organosilane precursor is SiH(NMe$_2$)$_2$(iPr-amd).

8. The Si-containing film forming composition of claim 1, wherein n=3, x=2, y=1, z=1, and the organosilane precursor has the formula:

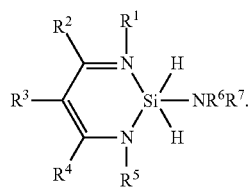

9. The Si-containing film forming composition of claim 8, wherein the organosilane precursor is selected from the group consisting of:

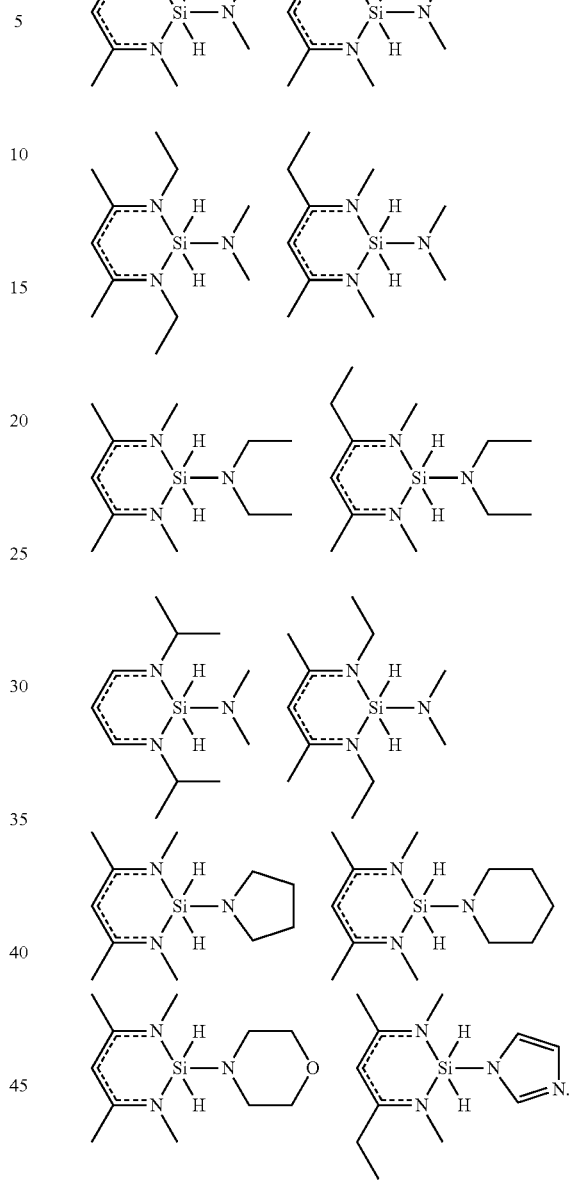

10. The Si-containing film forming composition of claim 1, wherein n=3, x=1, y=1, z=2, and the organosilane precursor has the formula:

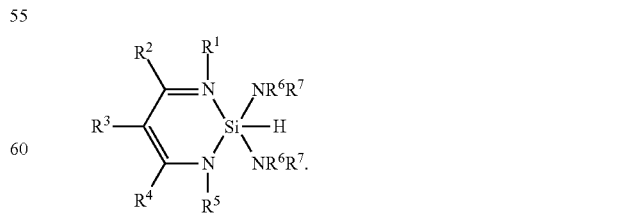

11. The Si-containing film forming composition of claim 1, wherein the organosilane precursor is selected from the group consisting of:

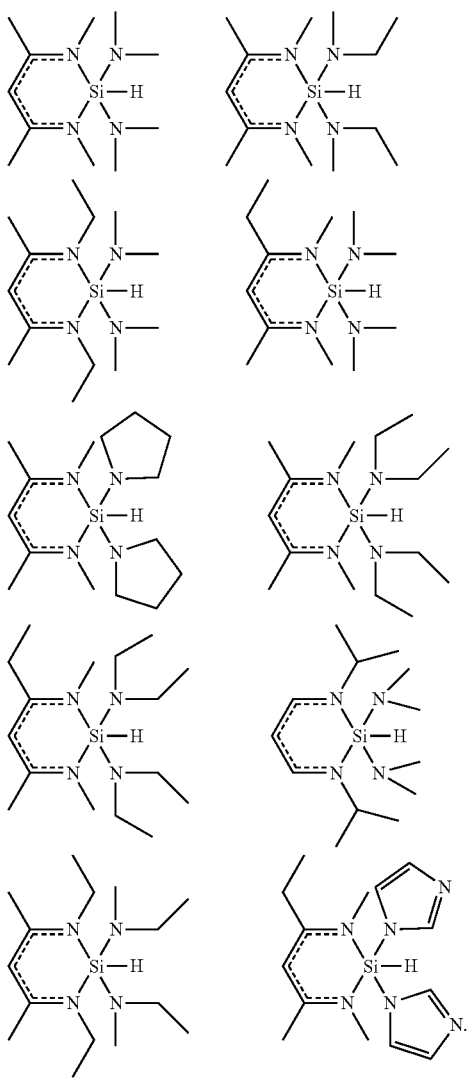

12. The Si-containing film forming composition of claim 1, wherein n=1, x=1, y=2, z=1, and the organosilane precursor has the formula:

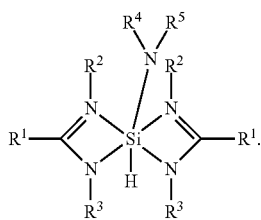

13. The Si-containing film forming composition of claim 12, wherein the organosilane precursor is selected from the group consisting of:

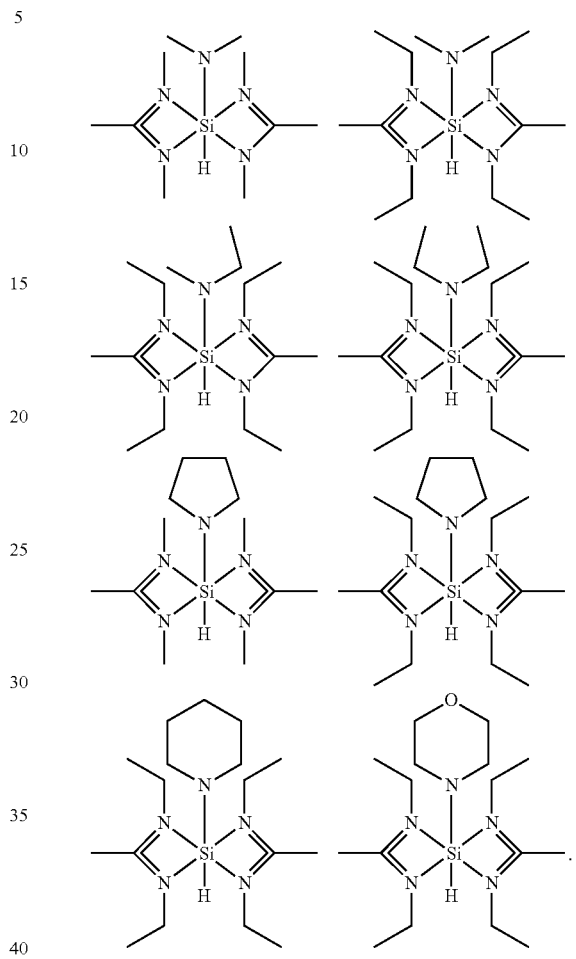

14. A method of depositing a Si-containing layer on a substrate, the method comprising:
 introducing a Si-containing film forming composition of claim 1 into a reactor having a substrate disposed therein; and
 depositing at least part of the organosilane precursor onto the substrate to form a Si-containing layer using a vapor deposition method.

15. The method of claim 14, further comprising introducing into the reactor a reactant, wherein the reactant is selected from the group consisting of $H_2$, $NH_3$, $(SiH_3)_3N$, hydridosilanes, chlorosilanes, chloropolysilanes, alkysilanes, hydrazines, organic amines, pyrazoline, pyridine, B-containing molecules, alkyl metals, radical species thereof, and mixtures thereof.

* * * * *